US010039509B2

(12) United States Patent
Okusu et al.

(10) Patent No.: US 10,039,509 B2
(45) Date of Patent: Aug. 7, 2018

(54) CONSOLE DEVICE OF PORTABLE TYPE, CONTROL METHOD AND RADIOGRAPHIC IMAGING SYSTEM

(71) Applicant: FUJIFILM Corporation, Tokyo (JP)

(72) Inventors: Kiyohisa Okusu, Kanagawa (JP); Yosuke Ohashi, Kanagawa (JP); Yuki Okabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 204 days.

(21) Appl. No.: 14/860,724

(22) Filed: Sep. 22, 2015

(65) Prior Publication Data

US 2016/0081642 A1    Mar. 24, 2016

(30) Foreign Application Priority Data

Sep. 22, 2014  (JP) ................................. 2014-192226

(51) Int. Cl.
*A61B 6/00* (2006.01)
*G06F 3/0482* (2013.01)
(Continued)

(52) U.S. Cl.
CPC ............ *A61B 6/465* (2013.01); *A61B 6/0407* (2013.01); *A61B 6/4208* (2013.01);
(Continued)

(58) Field of Classification Search
CPC ... A61B 6/0407; A61B 6/4208; A61B 6/4283; A61B 6/4452; A61B 6/46; A61B 6/461;
(Continued)

(56) References Cited

U.S. PATENT DOCUMENTS 4,160,906 A * 7/1979 Daniels .................. G05B 19/10
378/115
4,597,094 A * 6/1986 Kleinman .............. A61B 6/469
378/116
(Continued)

FOREIGN PATENT DOCUMENTS

JP     2002263088    9/2002
JP     2004157271    6/2004
(Continued)

OTHER PUBLICATIONS

"Office Action of Japan Counterpart Application" with English translation thereof, dated Dec. 7, 2016, pp. 1-6.

*Primary Examiner* — Allen C. Ho
(74) *Attorney, Agent, or Firm* — JCIPRNET

(57) ABSTRACT

A console device of a portable type is combined with a radiographic imaging device, and retrieves a radiation image from the radiographic imaging device. A registration unit selectively registers plural user menu options for retrieving the radiation image. A radiation image retrieving unit retrieves the radiation image according to a registered one of the user menu options. A display controller, after displaying the radiation image retrieved according to a current user menu option on a display unit among the user menu options, performs display processing of a succeeding user menu option for retrieving a succeeding radiation image in an overlapped manner with the displayed radiation image. Preferably, a pass-through area is formed in the radiation image by directly receiving the radiation without passing through an object. The display controller performs display processing of the current or succeeding user menu option inside the pass-through area.

15 Claims, 36 Drawing Sheets

(51) Int. Cl.
*G06F 3/0484* (2013.01)
*G06T 11/60* (2006.01)
*A61B 6/04* (2006.01)

(52) U.S. Cl.
CPC .......... *A61B 6/4283* (2013.01); *A61B 6/4452* (2013.01); *A61B 6/46* (2013.01); *A61B 6/461* (2013.01); *A61B 6/508* (2013.01); *A61B 6/56* (2013.01); *A61B 6/563* (2013.01); *A61B 6/566* (2013.01); *G06F 3/0482* (2013.01); *G06F 3/04845* (2013.01); *G06F 3/04847* (2013.01); *G06T 11/60* (2013.01); *G06T 2200/24* (2013.01); *G06T 2210/41* (2013.01)

(58) Field of Classification Search
CPC ........... A61B 6/465; A61B 6/508; A61B 6/56; A61B 6/563; A61B 6/566
USPC ............. 378/189, 196, 197, 62, 114–116, 98
See application file for complete search history.

(56) References Cited

U.S. PATENT DOCUMENTS

| | | | | |
|---|---|---|---|---|
| 5,608,774 A * | 3/1997 | Polichar | G01N 23/04 | 378/102 |
| 5,675,358 A * | 10/1997 | Bullock | G06F 3/033 | 345/419 |
| 5,737,386 A * | 4/1998 | Strawder | A61B 6/00 | 378/116 |
| 5,737,506 A * | 4/1998 | McKenna | G06F 19/324 | 345/427 |
| 5,926,165 A * | 7/1999 | Grewer | H04N 5/45 | 348/E5.112 |
| 5,949,811 A * | 9/1999 | Baba | A61B 6/4225 | 378/108 |
| 5,987,345 A * | 11/1999 | Engelmann | G06F 19/321 | 600/407 |
| 5,988,851 A * | 11/1999 | Gent | A61B 6/00 | 700/17 |
| 6,081,267 A * | 6/2000 | Stockham | G06F 19/321 | 378/98 |
| 6,233,310 B1 * | 5/2001 | Relihan | H05G 1/46 | 378/108 |
| 6,259,767 B1 * | 7/2001 | Neumann | A61B 6/06 | 378/110 |
| 6,463,121 B1 * | 10/2002 | Milnes | A61B 6/4482 | 378/62 |
| 6,469,717 B1 * | 10/2002 | Wineke | G06F 3/04845 | 715/765 |
| 6,484,048 B1 * | 11/2002 | Hoshino | G01R 33/4833 | 345/419 |
| 6,501,827 B1 * | 12/2002 | Takasawa | G06F 19/321 | 378/116 |
| 6,504,897 B1 * | 1/2003 | Yonekawa | A61B 6/00 | 378/57 |
| 6,508,586 B2 * | 1/2003 | Oota | A61B 6/032 | 378/194 |
| 6,542,579 B1 * | 4/2003 | Takasawa | A61B 6/00 | 378/162 |
| 6,671,394 B1 * | 12/2003 | Sako | A61B 6/469 | 250/370.09 |
| 6,714,623 B2 * | 3/2004 | Sako | A61B 6/00 | 378/115 |
| 6,762,429 B2 * | 7/2004 | Aonuma | A61B 6/463 | 250/582 |
| 6,819,785 B1 * | 11/2004 | Vining | G06F 17/30056 | 382/128 |
| 6,859,513 B2 * | 2/2005 | Sako | A61B 6/00 | 378/16 |
| 6,920,201 B2 * | 7/2005 | Maack | A61B 6/00 | 378/108 |
| 6,976,231 B1 * | 12/2005 | Funahashi | G06F 3/04845 | 715/853 |
| 6,993,114 B2 * | 1/2006 | Takasawa | G06F 19/3487 | 378/116 |
| 7,006,600 B1 * | 2/2006 | Krema | A61B 6/145 | 348/E5.086 |
| 7,010,091 B2 * | 3/2006 | Hayashida | G01T 1/17 | 250/370.09 |
| 7,023,959 B2 * | 4/2006 | Nakagawa | A61B 6/4405 | 378/98 |
| 7,106,479 B2 * | 9/2006 | Roy | G06F 19/321 | 358/3.27 |
| 7,120,229 B2 * | 10/2006 | Takasawa | A61B 6/00 | 378/108 |
| 7,130,377 B2 * | 10/2006 | Matsuno | A61B 6/4225 | 378/116 |
| 7,203,270 B2 * | 4/2007 | Okumura | A61B 6/032 | 378/109 |
| 7,239,733 B2 * | 7/2007 | Abe | G06T 7/60 | 345/660 |
| 7,502,445 B2 * | 3/2009 | Shi | A61B 6/032 | 378/115 |
| 7,561,668 B2 * | 7/2009 | Ohta | G03B 42/04 | 378/102 |
| 7,684,597 B2 * | 3/2010 | Kawano | G06T 5/009 | 378/16 |
| 7,684,605 B2 * | 3/2010 | Klingenbeck-Regn | A61B 6/00 | 378/62 |
| 7,689,266 B2 * | 3/2010 | Shinohara | A61B 6/00 | 378/4 |
| 7,737,427 B2 * | 6/2010 | Kito | A61B 6/4233 | 250/370.08 |
| 7,751,529 B2 * | 7/2010 | Ohara | A61B 6/00 | 378/116 |
| 7,852,332 B2 * | 12/2010 | Sako | A61B 6/463 | 345/419 |
| 7,889,843 B2 * | 2/2011 | Watanabe | A61B 6/4216 | 250/370.09 |
| 7,979,287 B2 * | 7/2011 | Amitani | A61B 6/00 | 378/197 |
| 8,021,045 B2 * | 9/2011 | Foos | A61B 6/4405 | 378/162 |
| 8,077,828 B2 * | 12/2011 | Aoyama | A61B 6/465 | 378/108 |
| 8,107,590 B2 * | 1/2012 | Nishino | A61B 6/00 | 250/370.09 |
| 8,121,257 B2 * | 2/2012 | Takasawa | A61B 6/542 | 378/115 |
| 8,270,570 B2 * | 9/2012 | Matsumoto | A61B 6/00 | 378/101 |
| 8,275,835 B2 * | 9/2012 | Eguchi | A61B 6/4233 | 378/189 |
| 8,494,247 B2 * | 7/2013 | Watanabe | A61B 6/00 | 378/115 |
| 8,526,573 B2 * | 9/2013 | Ferro, Jr. | A61B 6/4429 | 378/62 |
| 8,550,709 B2 * | 10/2013 | Nishino | A61B 6/04 | 378/145 |
| 8,621,213 B2 * | 12/2013 | Logan | G06F 19/321 | 370/352 |
| 8,654,925 B2 * | 2/2014 | Nishino | A61B 6/4405 | 378/115 |
| 8,681,116 B2 * | 3/2014 | Merritt | A61B 5/7445 | 345/173 |
| 8,744,043 B2 * | 6/2014 | Ohta | A61B 6/06 | 378/62 |
| 8,748,834 B2 * | 6/2014 | Enomoto | A61B 6/4233 | 250/370.08 |
| 8,785,863 B2 * | 7/2014 | Oda | G01T 1/17 | 250/366 |
| 8,948,543 B2 * | 2/2015 | Koishi | G06K 9/2027 | 382/132 |
| 8,976,931 B2 * | 3/2015 | Lalena | A61B 6/4405 | 378/98.5 |
| 9,134,436 B2 * | 9/2015 | Kwak | A61B 6/4266 | |
| 9,168,011 B2 * | 10/2015 | Nenoki | A61B 6/4283 | |
| 9,204,855 B2 * | 12/2015 | Tsubota | A61B 6/563 | |
| 9,265,467 B2 * | 2/2016 | Kamiya | A61B 6/5241 | |

(56) References Cited

U.S. PATENT DOCUMENTS

| | | | |
|---|---|---|---|
| 9,295,438 B2 | 3/2016 | Omura et al. | |
| 9,313,868 B2 * | 4/2016 | Arima | H05G 1/30 |
| 9,320,482 B2 * | 4/2016 | Tajima | A61B 6/42 |
| 9,357,974 B2 * | 6/2016 | Foos | A61B 6/4405 |
| 9,398,887 B2 * | 7/2016 | Miyazawa | G06F 19/321 |
| 9,402,592 B2 * | 8/2016 | Garcia | A61B 6/4283 |
| 9,405,183 B2 * | 8/2016 | Ando | A61B 6/4266 |
| 9,492,134 B2 * | 11/2016 | Takasaki | A61B 6/5205 |
| 9,492,137 B2 * | 11/2016 | Iwamoto | A61B 6/4283 |
| 9,498,173 B2 * | 11/2016 | Yamada | A61B 6/4405 |
| 9,514,275 B2 * | 12/2016 | Profio | A61B 6/465 |
| 9,538,978 B2 * | 1/2017 | Makino | A61B 6/563 |
| 9,554,762 B2 * | 1/2017 | Kim | A61B 6/48 |
| 9,600,882 B2 * | 3/2017 | Mankovich | G06T 19/00 |
| 9,655,575 B2 * | 5/2017 | Park | A61B 6/461 |
| 9,665,254 B2 * | 5/2017 | Hayashi | A61B 6/5294 |
| 9,710,146 B2 * | 7/2017 | Tokunaga | G06F 3/04855 |
| 9,730,658 B2 * | 8/2017 | Tajima | A61B 6/4283 |
| 9,892,521 B2 * | 2/2018 | Enomoto | G06T 7/30 |
| 2005/0041844 A1 | 2/2005 | Yamanaka | |
| 2009/0268864 A1 | 10/2009 | Nishida | |

FOREIGN PATENT DOCUMENTS

| | | |
|---|---|---|
| JP | 2004194979 | 7/2004 |
| JP | 2005065944 | 3/2005 |
| JP | 2009-089723 | 4/2009 |
| JP | 2013225380 | 10/2013 |
| JP | 2014064776 | 4/2014 |
| JP | 2014155620 | 8/2014 |
| WO | 2006129433 | 12/2006 |

\* cited by examiner

F I G. 12
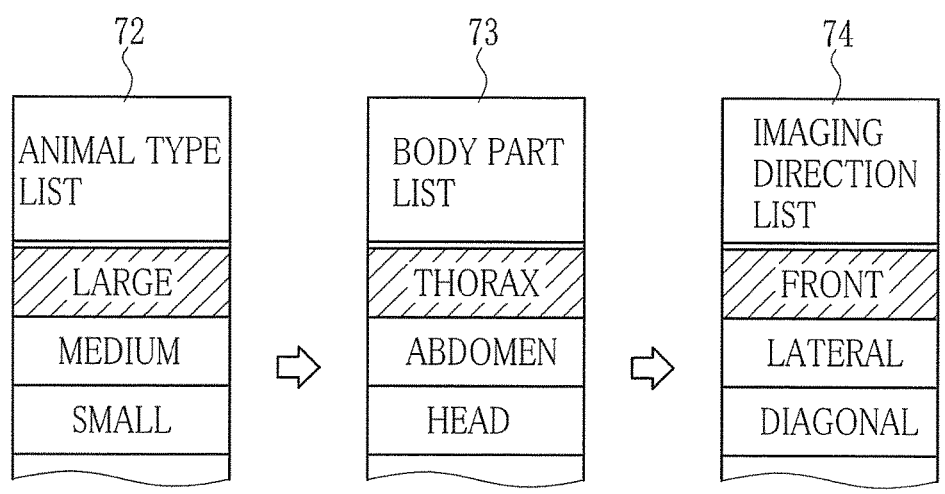

F I G . 21
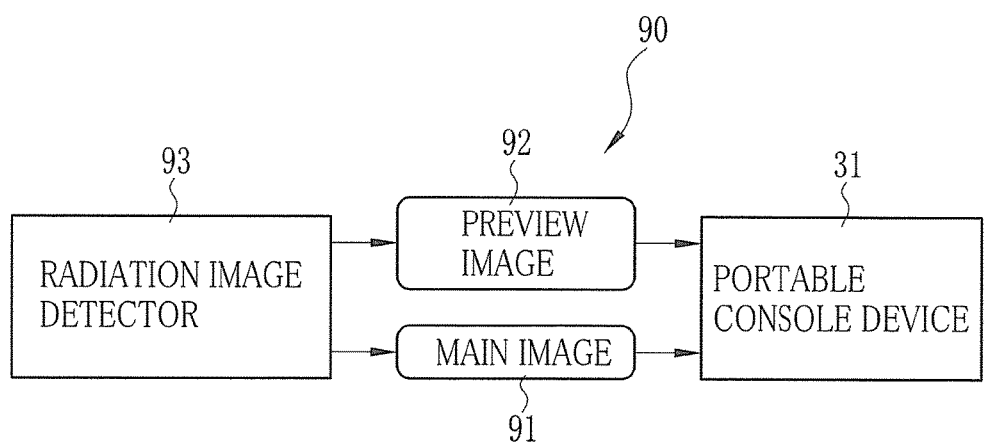

FIG. 23
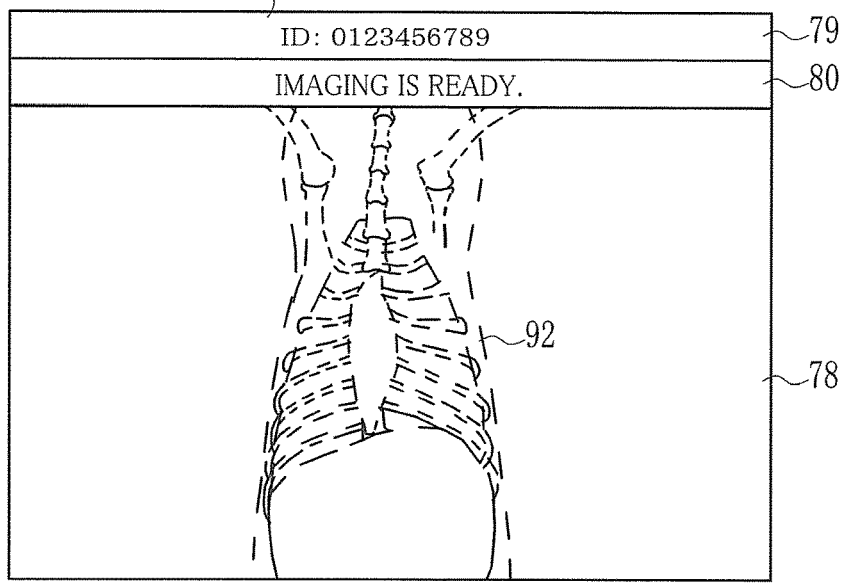
 RECEIVE MAIN IMAGE
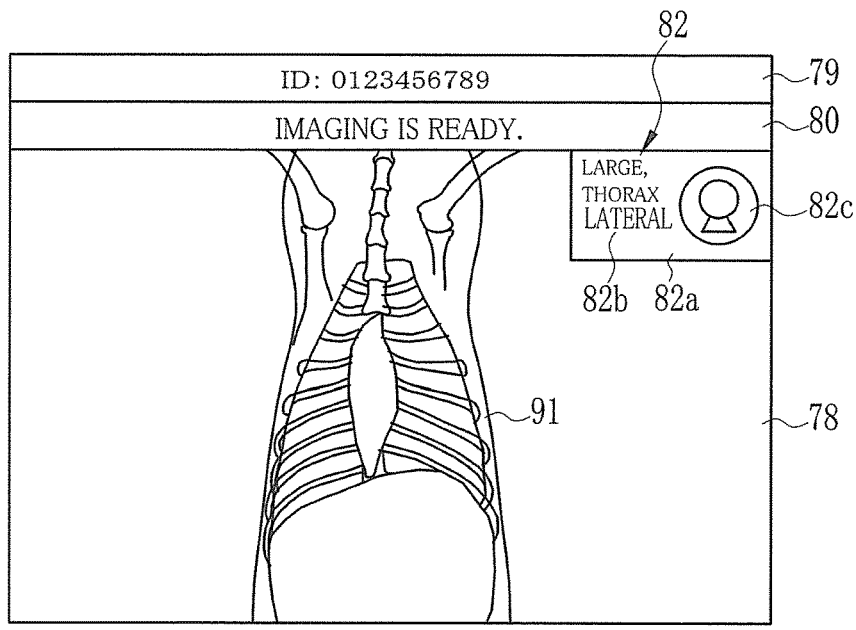

FIG. 27
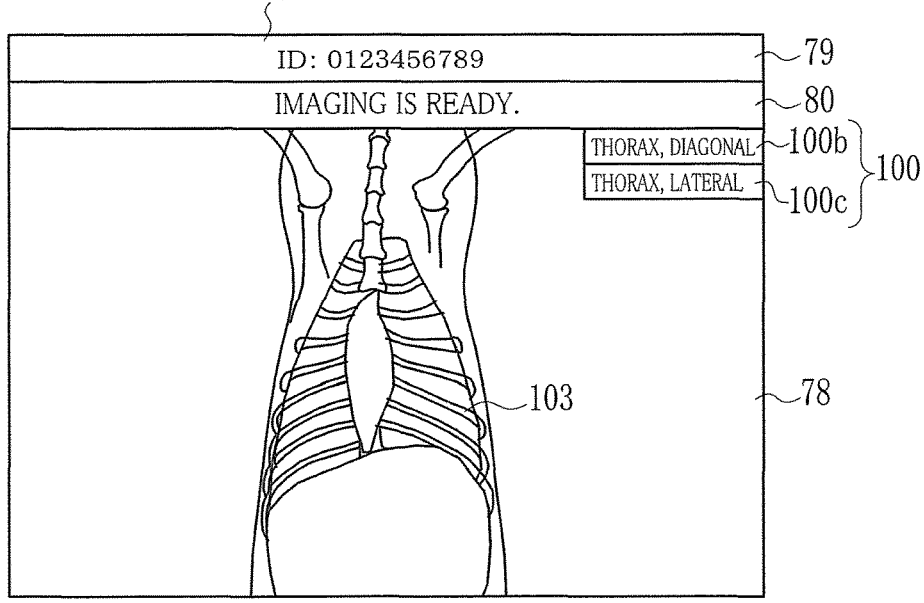
 RECEIVE IMAGE OF FINAL SUB MENU ITEM
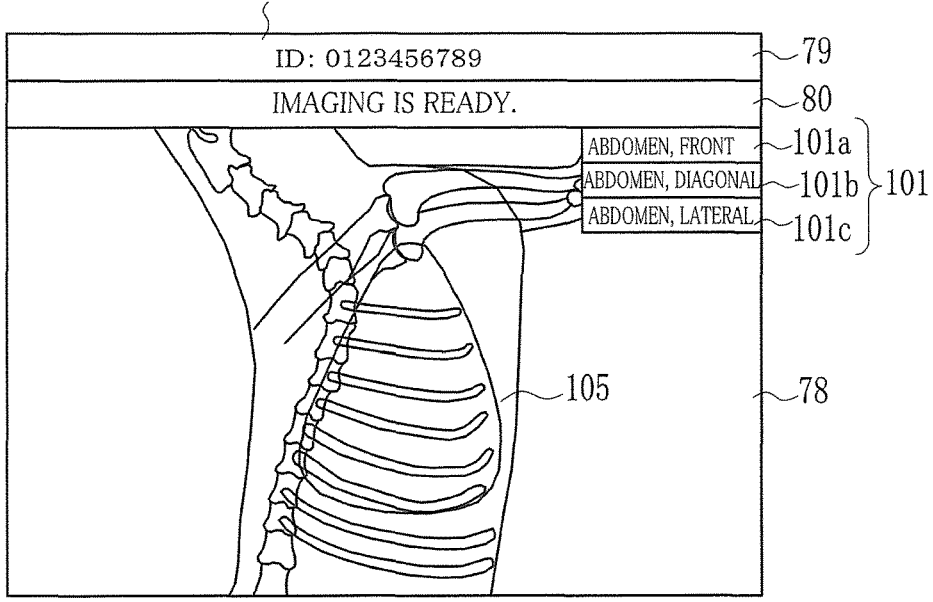

FIG. 29
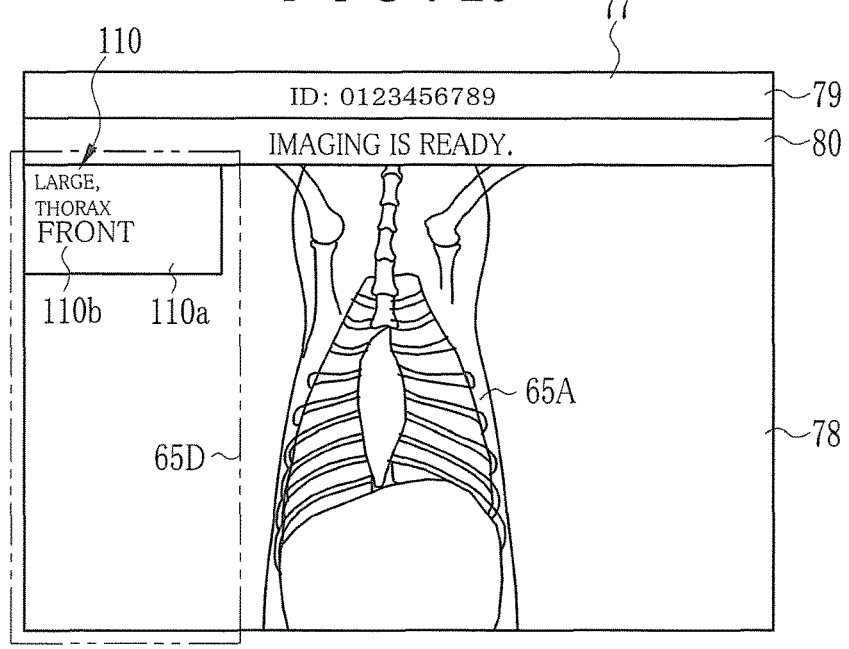
 LAPSE OF WAITING TIME
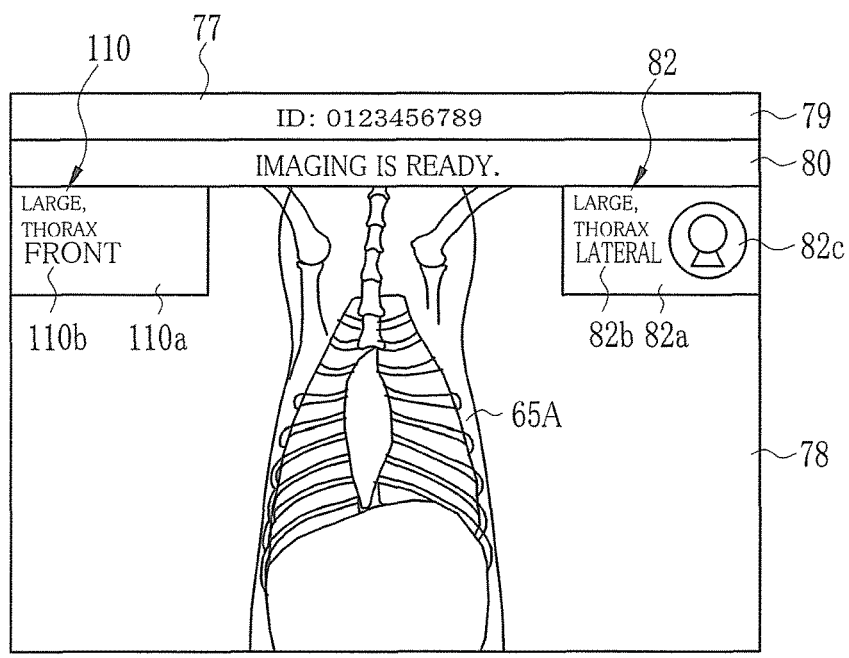

FIG. 31
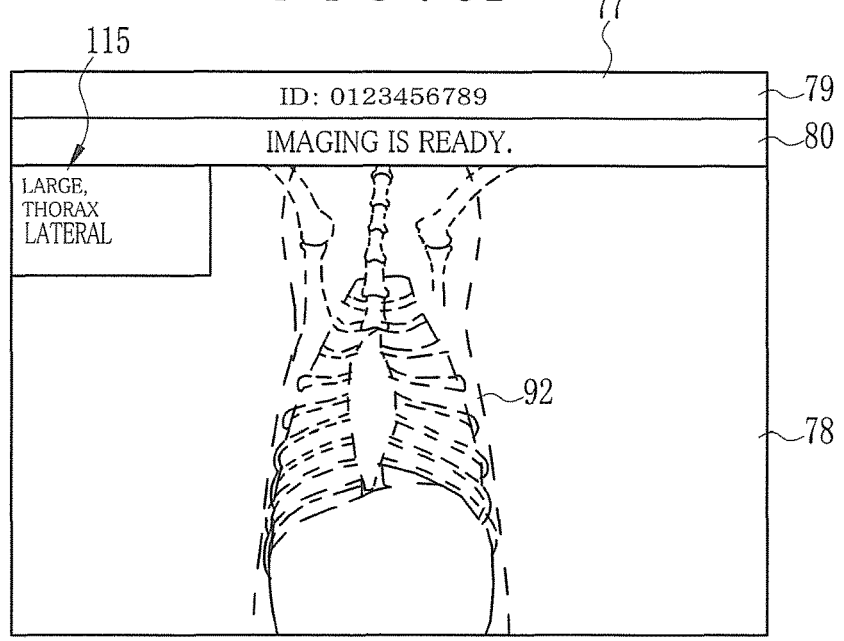
⇩ RECEIVE MAIN IMAGE
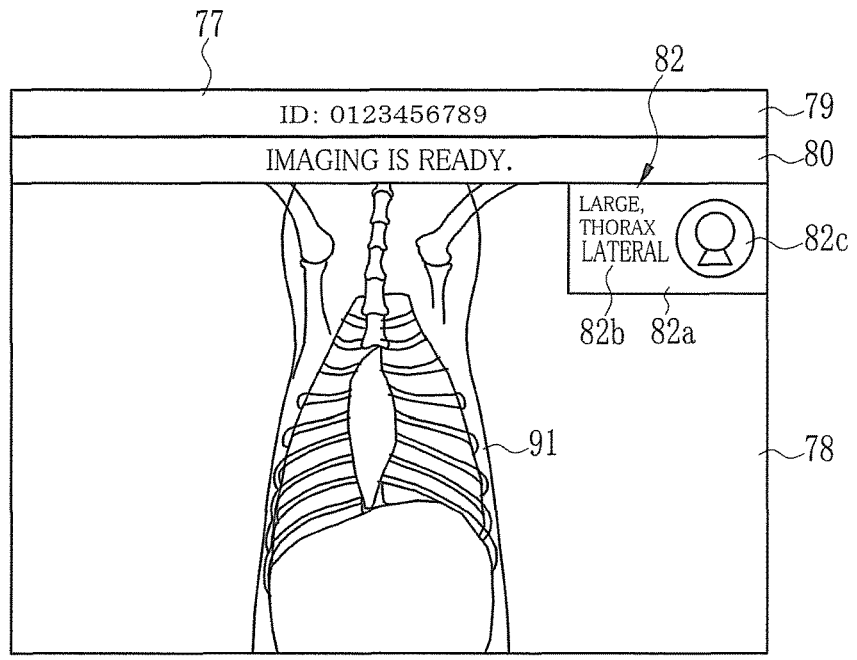

FIG. 36
ID: 0123456789
IMAGING IS READY.
STEP 1
PLACE...
HOLD...
IN CASE OF...
NB. A RABBIT HAS BEHAVIOR...
STEP 2
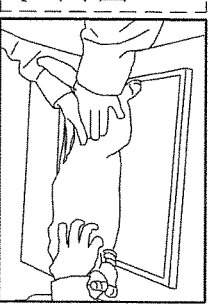
TURN ROUND...
PULL...
DIRECT...

CONSOLE DEVICE OF PORTABLE TYPE, CONTROL METHOD AND RADIOGRAPHIC IMAGING SYSTEM

CROSS-REFERENCE TO RELATED APPLICATION

This application claims priority under 35 USC 119 from Japanese Patent Application No. 2014-192226, filed 22 Sep. 2014, the disclosure of which is incorporated by reference herein.

BACKGROUND OF THE INVENTION

1. Field of the Invention

The present invention relates to a console device of a portable type, a control method and a radiographic imaging system. More particularly, the present invention relates to a console device of a portable type in which suitability for visual recognition of an image is improved, and a control method and a radiographic imaging system.

2. Description Related to the Prior Art

In the field of medicine, image diagnosis is performed by acquiring medical images of a patient. To this end, a radiographic imaging system for use with radiation such as X-rays is well-known as a system for acquiring medical images. The radiographic imaging system includes a radiation generator and a radiographic imaging apparatus. The radiation generator generates radiation. The radiographic imaging apparatus forms a radiation image of a body of a patient by detecting the radiation transmitted through the body. The radiation generator includes a radiation source, source driver and radiation switch. The radiation source applies the radiation to the body. The source driver drives and controls the radiation source. The radiation switch is operable to send an input to the source driver for starting the radiation source. The radiographic imaging apparatus includes a radiographic imaging device and a console device, which retrieves (or reads) radiation images recorded by the radiographic imaging device and performs display processing for a display to display the radiation image.

There is a type of radiographic imaging device in which a radiation film or an imaging plate (IP) coated with photostimulable phosphor is used for recording a radiation image. The radiation image on the radiation film or the like is read by a scanner for the radiation film or an IP reading apparatus, and converted into image data. The console device retrieves the converted image data, and displays an image of the image data. Also, a known type of radiographic imaging device is a radiation image detector, which converts radiation into an electric signal to record a radiation image. The radiation image detector includes a sensor panel called a flat panel detector (FPD), which converts the radiation transmitted through a body of the patient into an electric signal, to detect the radiation image. As the radiation image detector can transmit the radiation image to the console device immediately for the console device to display the image. There is an advantage of visually checking the present image immediately after imaging, in comparison with the conventional type of the radiographic imaging device for use with the radiation film or imaging plate.

A widely available form of the console device of the desktop type includes a display panel and a console main unit. The display panel is a display unit for displaying a user menu option or radiation image retrieving menu option for retrieving a radiation image, and the retrieved radiation image. The user menu option displays a body part, imaging direction and the like related to imaging of a radiation image in a form of letters, icons and the like. The console main unit is based on a personal computer, workstation or other electronic terminal equipment, and retrieves a radiation image created by the radiographic imaging device. Also, the console main unit is a display controller or display processor for driving the display panel to display the user menu option and the radiation image together.

JP-A 2009-089723 discloses the radiographic imaging apparatus having a portable console device, which is based on a portable information terminal device such as a smart phone or tablet terminal device. The portable console device has a touchscreen display unit for displaying an image and receiving inputs in response to touch. The touchscreen display unit displays the user menu option and the radiation image in the same manner as the console device of the desktop type. The portable console device has a smaller size and smaller weight than the desktop type, and is operable in a manually held state in a hand of an operator. The portable console device is useful in various fields of health care in which an operator must work in an erect posture, for example, in a veterinary clinic, or for emergency medicine in which rapidity is essential.

In a veterinary clinic, a portable console device may be used in a placed state at a location distant from a veterinarian, for example, may be leaned on a special stand, or supported on a wall of a support plate. This is because the portable console device may be broken by abrupt motion of an animal with an animal body to be imaged for a radiation image, or may be made dirty by body fluid from the animal. It is possible in the veterinary clinic to create a plurality of the radiation image by manually holding the animal in predetermined positions, or by suitably changing a position of the animal for consecutive imaging. The portable console device is used in the placed state on a stationary support similarly.

Although the portable console device is useful in the human medicine, typically for emergency medicine or in-patient care in a hospital, it is necessary for medical staff manually to support a body of a bedridden patient assuming that he or she cannot stand alone. For this purpose, the portable console device is used also in the placed state on a stationary support.

It is preferable to display the radiation image in a large size on a touchscreen display unit, for example, in a full-screen size, for enabling viewing the radiation image even from a distant location because of the use of the portable console device at the distant location from the veterinarian or operator. The radiation image must be displayed for checking typically in consecutive imaging for plural images, because positioning or the like is checked after each event of imaging before creating another image.

It is conceivable to view to the radiation image from a distant location for the purpose of consecutive imaging of the animal by changing a position of the animal according to a user menu option or radiation image retrieving menu option. However, a size of the touchscreen display unit of the portable console device is smaller than that for a console device of a desktop type. Display sizes of the user menu option and the radiation image must be small in order to display the user menu option and the radiation image together within the touchscreen display unit, to lower suitability for visual recognition.

In JP-A 2009-089723, there is no suggestion of suitably keeping visual recognition of the user menu option for the radiation image on the display of the portable console device.

SUMMARY OF THE INVENTION

In view of the foregoing problems, an object of the present invention is to provide a console device of a portable type in which suitability for visual recognition of an image is improved, and a control method and a radiographic imaging system.

In order to achieve the above and other objects and advantages of this invention, a console device of a portable type for retrieving a radiation image created by a radiographic imaging device is provided. A registration unit registers plural user menu options for retrieving the radiation image. A radiation image retrieving unit retrieves the radiation image respectively according to the registered user menu options. A display controller, after displaying the radiation image retrieved according to a current user menu option on a display unit among the user menu options, performs display processing to display a succeeding user menu option for retrieving at least a succeeding radiation image in an overlapped manner with the displayed radiation image.

Preferably, the display controller performs display processing of the succeeding user menu option upon lapse of waiting time for display after the radiation image becomes displayed.

Preferably, the display controller causes the display unit to display a main image of the radiation image and a preview image of the radiation image with a smaller data size than the main image in a sequence of changing over from the preview image to the main image. Upon changing over the display unit from the preview image to the main image, the succeeding user menu option is displayed in an overlapped manner with the main image.

Preferably, the succeeding user menu option is constituted by a group of plural sub menu items, and the display controller performs display processing of the plural sub menu items by the group in a form of the succeeding user menu option.

Preferably, the display controller performs display processing to display the current user menu option in an overlapped manner with the radiation image.

Preferably, the display controller causes the display unit to display the current user menu option in an overlapped manner with the preview image. Upon changeover from the preview image to the main image, the succeeding user menu option is displayed in an overlapped manner with the main image.

Preferably, a pass-through area is formed in the radiation image by directly receiving the radiation without passing through an object. The display controller performs display processing of the current or succeeding user menu option inside the pass-through area.

Preferably, the display controller determines a display form of the current or succeeding user menu option within the pass-through area by considering a form of the pass-through area.

Preferably, the display controller reads out attribute information associated with the radiation image before displaying the current user menu option, and causes display processing to display a first item in an overlapped manner with the current user menu option, the first item being relevant to the current user menu option among plural items included in the attribute information.

Preferably, the display unit is changed over from the succeeding user menu option to another user menu option, the radiation image retrieving unit changes a sequence of retrieving the radiation image.

Preferably, assuming that the succeeding user menu option is changed to a current user menu option, the radiation image retrieving unit enables the radiographic imaging device to perform re-imaging according to the current user menu option.

Preferably, furthermore, an audio processing unit notifies information of the succeeding user menu option acoustically.

Preferably, the display controller causes the display unit to display guidance information for steps of creating the radiation image in the radiographic imaging device until the radiation image is initially retrieved according to the plural user menu options.

Preferably, an object in the radiation image is an animal body, and the radiation image is for veterinary use.

Also, a control method for a portable information terminal device for retrieving a radiation image created by a radiographic imaging device is provided. In the control method, plural user menu options for retrieving the radiation image are registered. The radiation image is retrieved respectively according to the registered user menu options. After displaying the radiation image retrieved according to a current user menu option on a display unit among the user menu options, a succeeding user menu option for retrieving at least a succeeding radiation image is displayed in an overlapped manner with the displayed radiation image.

Also, a radiographic imaging system is provided, and a radiographic imaging device for creating a radiation image from radiation passed through a body. A console device of a portable type retrieves the radiation image from the radiographic imaging device. A console holder holds the console device. The console device includes a registration unit for registering plural user menu options for retrieving the radiation image. A radiation image retrieving unit retrieves the radiation image respectively according to the registered user menu options. A display controller, after displaying the radiation image retrieved according to a current user menu option on a display unit among the user menu options, performs display processing to display a succeeding user menu option for retrieving at least a succeeding radiation image in an overlapped manner with the displayed radiation image.

Consequently, suitability for visual recognition of an image is improved, because a succeeding user menu option for a succeeding radiation image is displayed in an overlapped manner with the displayed radiation image.

BRIEF DESCRIPTION OF THE DRAWINGS

The above objects and advantages of the present invention will become more apparent from the following detailed description when read in connection with the accompanying drawings, in which:

FIG. 12 is a chart illustrating a list displayed in menu registration;

FIG. 21 is a block diagram schematically illustrating a radiographic imaging device of a second preferred embodiment;

FIG. 23 is an explanatory view illustrating a view page;

FIG. 27 is an explanatory view illustrating a view page;

FIG. 29 is an explanatory view illustrating a view page;

FIG. 31 is an explanatory view illustrating a view page;

FIG. 36 is a plan illustrating a view page;

DETAILED DESCRIPTION OF THE PREFERRED EMBODIMENT(S) OF THE PRESENT INVENTION

First Embodiment

Figure 1:
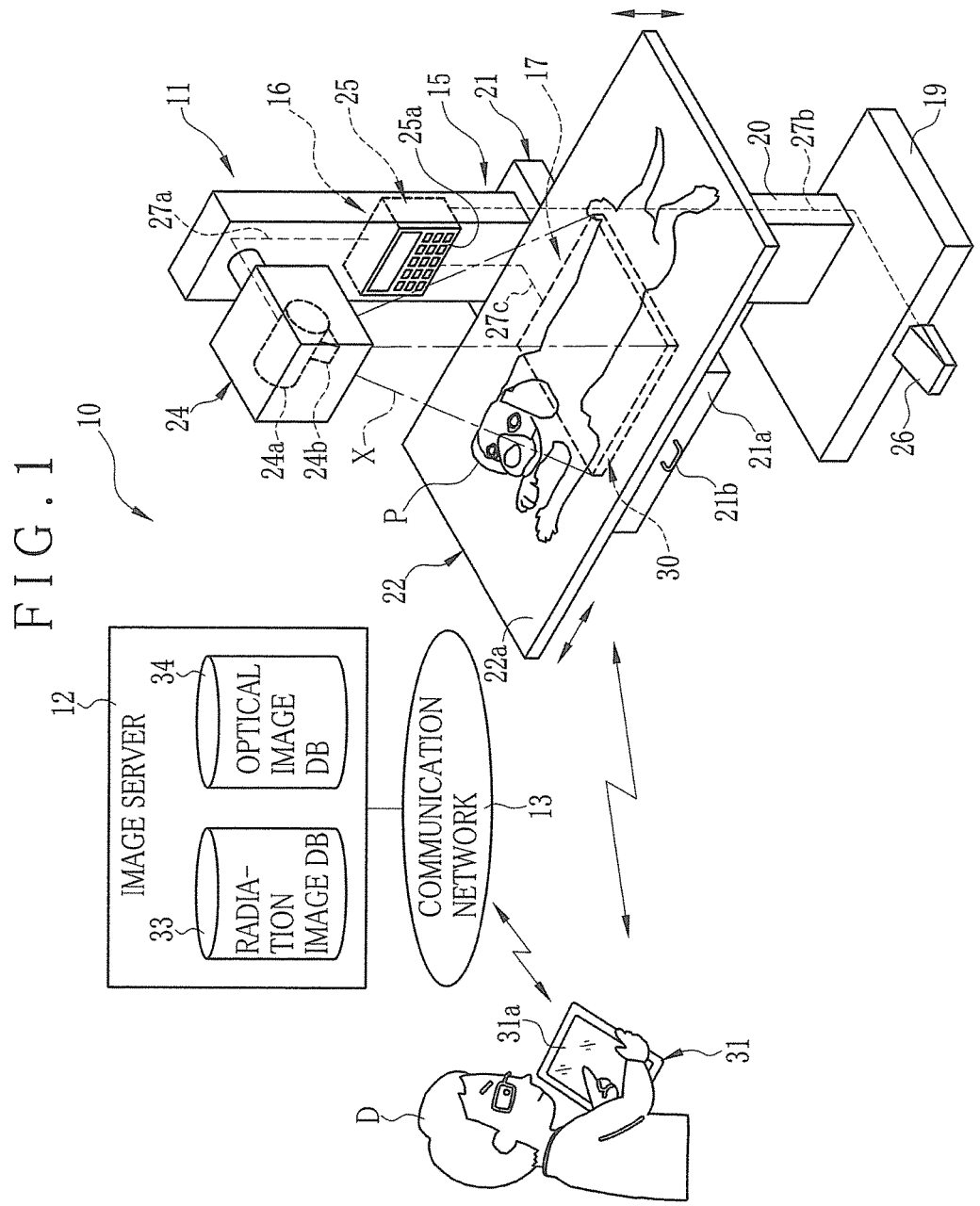
FIG. 1 is a perspective view illustrating a radiographic imaging system for veterinary use.

In FIG. 1, a radiography system architecture 10 or X-ray system architecture for veterinary use is illustrated, and used for imaging of an animal body P of an animal, for example, a dog, cat, and various pets and small animals. The radiography system architecture 10 includes a radiographic imaging system 11 or radiographic imaging apparatus for veterinary use, an image server 12 and a communication network 13. The radiographic imaging system 11 forms a radiation image of the animal body P. The image server 12 manages radiation images of the animal body P. The communication network 13 interconnects the radiographic imaging system 11 and the image server 12 in a communicable manner. An example of the communication network 13 is a local area network (LAN) installed in a veterinary clinic.

The radiographic imaging system 11 is installed in an examination room in the veterinary clinic. The radiographic imaging system 11 includes a stand device 15, a radiation generator 16 or X-ray generator, and a radiographic imaging device 17 or X-ray imaging device. A patient table 22 of the stand device 15 supports an animal body P of an animal to be imaged. The radiation generator 16 emits radiation. The radiographic imaging device 17 forms a radiation image by receiving the radiation transmitted through the animal body P. The radiation generator 16 and the radiographic imaging device 17 are partially incorporated in the stand device 15. A portable console device 31 for veterinary use in the radiographic imaging system 11 is operated by a veterinarian D or operator, and can be carried and moved with portability in a site of the veterinary clinic.

The stand device 15 includes a base portion 19, a stand 20 (support post), a lift mechanism 21 and the patient table 22. The base portion 19 is placed on a floor of an examination room, and supports the entirety of the stand device 15 as a pedestal. The stand 20 is fixed on the base portion 19 to extend vertically as a pillar, to support the patient table 22.

The lift mechanism 21 is a mechanism for supporting the patient table 22, and disposed on the stand 20 in a manner movable up and down vertically. A radiation image detector 30 or electronic cassette is included in the radiographic imaging device 17. A detector holder 21a is disposed in the lift mechanism 21 for containing the radiation image detector 30. A grip handle 21b is formed on a front surface of the detector holder 21a, and used for pulling out the detector holder 21a from a lower side of the patient table 22. An inner space of the detector holder 21a contains the radiation image detector 30. Returning the detector holder 21a with the radiation image detector 30 to the lower side of the patient table 22 positions the radiation image detector 30 under the patient table 22.

The patient table 22 is used for placement of the animal body P. An upper surface 22a of the patient table 22 is kept horizontal by supporting the patient table 22 with the lift mechanism 21. The patient table 22 is in a shape of a rectangular quadrilateral extending in a horizontal direction. The lift mechanism 21 keeps the patient table 22 movable horizontally in its longitudinal direction. Moving the patient table 22 with the animal body P causes a body part of the animal body P to face the radiation image detector 30.

The radiation generator 16 includes a radiation source 24 or X-ray source, a source driver 25 and a radiation switch 26. The radiation source 24 applies radiation or X-rays to the animal body P on the patient table 22. The source driver 25 controls the radiation source 24. Signal cables 27a and 27b are extended into the base portion 19 and the stand 20, and used to connect the radiation source 24 and the radiation switch 26 to the source driver 25.

The radiation source 24 is supported on an upper portion of the stand 20 and opposed to the patient table 22. The radiation source 24 includes an X-ray tube 24a and a collimator 24b. The X-ray tube 24a emits X-rays X as radiation. The collimator 24b limits a radiation field of radiation from the X-ray tube 24a.

The source driver 25 generates a control signal according to an imaging condition and controls the radiation source 24 by use of the control signal. Values in the imaging condition are a tube voltage, tube current, irradiation time and the like. The tube voltage determines energy spectrum of the radiation. The tube current determines dose of the radiation per unit time. The irradiation time is time of continuing the irradiation of the radiation. The control signal is transmitted by the signal cable 27a to the radiation source 24. A control panel 25a is disposed in the source driver 25 for setting the imaging condition. The control panel 25a includes plural buttons and a display panel. The buttons are used for setting the imaging condition. The display panel displays the imaging condition. The source driver 25 is disposed in the stand 20. The control panel 25a appears externally through the front side of the stand 20. The source driver 25 is disposed between the patient table 22 and the radiation source 24 for the veterinarian to touch the control panel 25a while he or she keeps the animal body P placed on the patient table 22.

The radiation switch 26 is a foot pedal type of switch. A veterinarian D or operator can depress the radiation switch 26 with his or her foot while he or she holds the animal body P on the patient table 22 with both hands. The radiation switch 26 generates a start signal for starting the radiation source 24 to emit radiation. The start signal of the radiation switch 26 is input to the source driver 25 through the signal cable 27b.

The source driver 25 controls the radiation source 24 according to a signal from the radiation switch 26. In case a start signal is received from the radiation switch 26, the source driver 25 starts supplying the radiation source 24 with power, to drive the radiation source 24 to emit radiation. At the same time as the start, the source driver 25 starts a timer to measure irradiation time or elapsed time. In case the elapsed time becomes as long as a predetermined duration according to the imaging condition, the irradiation of the radiation is stopped. The irradiation time of the radiation is changeable according to an irradiation condition. In the source driver 25, longest tolerable time for safety of the irradiation is predetermined. The irradiation time according to the irradiation condition is set within a range of the longest tolerable time.

Figure 3:
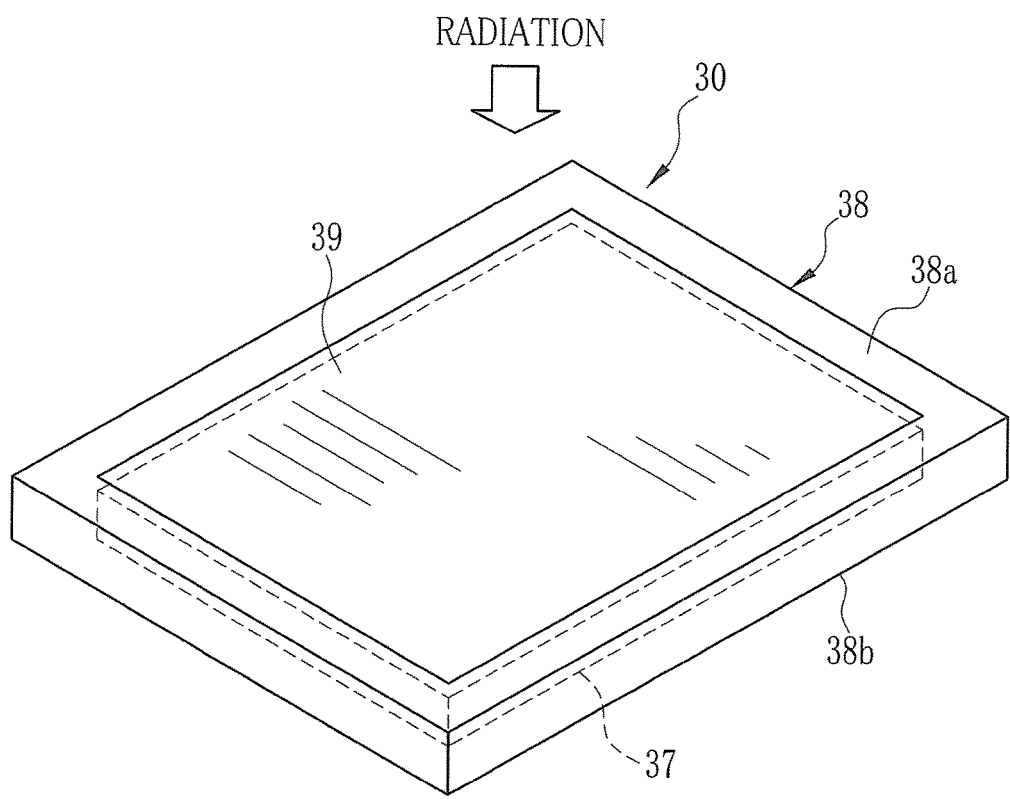
FIG. 3 is a perspective view illustrating a radiographic imaging device.

The radiographic imaging device 17 includes the radiation image detector 30 and the portable console device 31 for veterinary use. The radiation image detector 30 detects a radiation image. The portable console device 31 is a user terminal device in connection with the radiation image detector 30, for acquiring and displaying the radiation image. A portable housing 38 in FIG. 3 is included in the radiation image detector 30, and has a flat shape with a small thickness in a quadrilateral shape. The housing 38 is in a form according to the International Standards ISO 4090: 2001 for a film cassette of IP cassette (imaging plate cassette). The radiation image detector 30 is generally referred to as an electronic cassette. A sensor panel 37 in FIG. 3 is contained in the housing 38, and converts radiation transmitted through the animal body P into an electric signal, to detect the radiation image.

A signal cable 27c in the stand device 15 connects the radiation image detector 30 to the source driver 25. The radiation image detector 30 receives the imaging condition and sync signals from the source driver 25 through the signal cable 27c. The imaging condition is utilized for setting a condition of the signal processing in the sensor panel 37 at the time of detecting a radiation image. The sync signals include a start flag signal for notifying a start of irradiation of the radiation source 24, and an end flag signal for notifying an end of the irradiation. The sensor panel 37 starts detecting of the radiation image in response to the start flag signal, and ends the detection of the radiation image in response to the end flag signal. The radiation image detector 30 transmits the detected radiation image to the portable console device 31.

The portable console device 31 is constituted by a tablet terminal device. A touchscreen display unit 31a or touchscreen interface (touch panel) is disposed in a front wall of the portable console device 31 for display and touch operation. The touchscreen display unit 31a corresponds to a display unit of the invention. The portable console device 31 is connected to the radiation image detector 30 and the communication network 13 in a communicable manner by radio communication. The portable console device 31 has a small size, small weight and high portability remarkably in comparison with a desktop type of console device being available widely. It is possible for a veterinarian or operator to carry the portable console device 31 in a veterinary clinic and operate the portable console device 31 easily with his or her hands.

Figure 2:
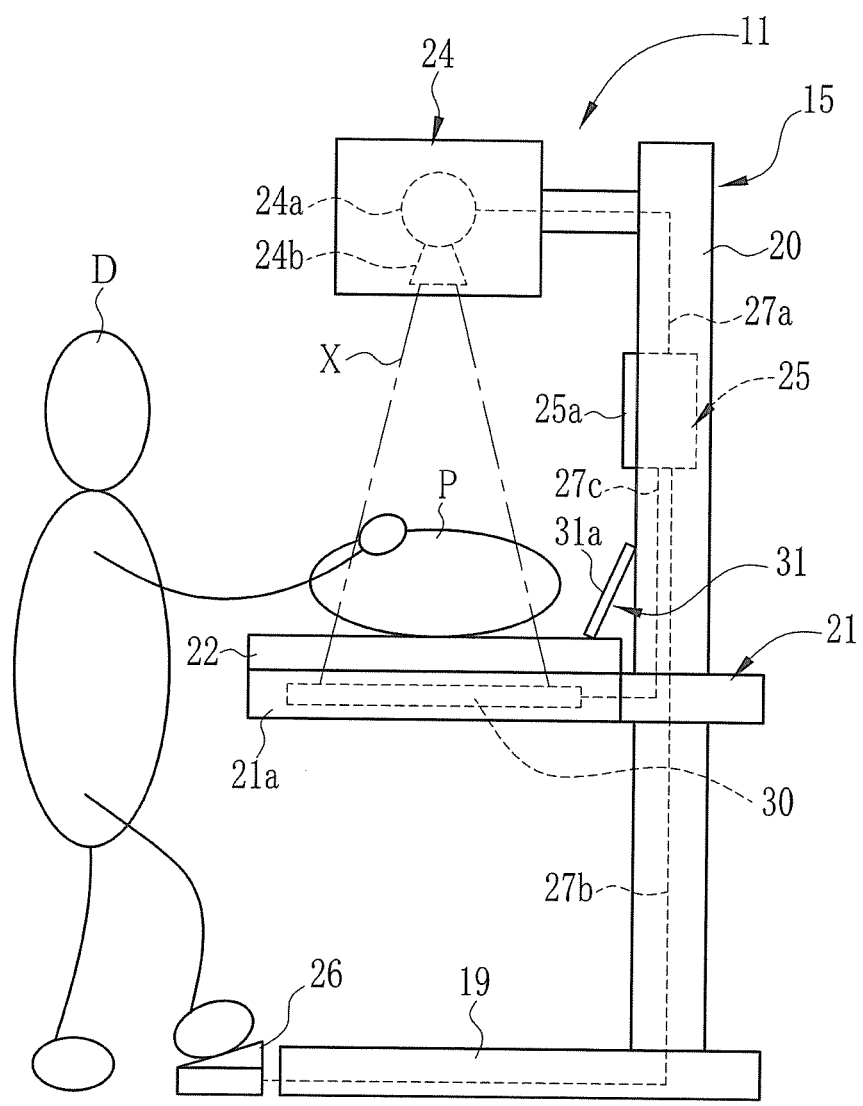
FIG. 2 is a side elevation illustrating the radiographic imaging system.

In FIG. 2, the portable console device 31 may be oriented in an erect posture at a distance from the veterinarian D or operator, typically in case he or she keeps the animal body P placed on the patient table 22 for radiographic imaging. In the drawing, the portable console device 31 is leaned on the patient table 22 for positioning. However, the portable console device 31 can be positioned on a support plate or the like near to the stand device 15, for example, in case the animal body P is very likely to move abruptly, in case the portable console device 31 may be made dirty by body liquid or the like from the animal.

The portable console device 31 is operable in two operation modes including an image browsing mode and an image viewing mode. In the image browsing mode, images are read out and browsed. In the image viewing mode, radiation images of past image browsing are viewed. The portable console device 31 is set in a selected one of the image browsing mode and image viewing mode, and used for the image browsing or viewing radiation images.

The portable console device 31 set in the image browsing mode receives an input of a body ID for identifying the animal body P and receives registration of a user menu option for retrieving a radiation image. The body ID and the user menu option are displayed on the touchscreen display unit 31a. As information with relevancy to the imaging of the radiation image in registering the user menu option, animal type information and imaging information is set in relation to the animal body P and the imaging. The animal type information includes information of animal types such as a dog, cat, bird, reptile and the like, and information of size of the animal body. The imaging information includes information of body parts such as a thorax, abdomen and head, and information of imaging directions such as front, lateral and diagonal directions. The animal type information and imaging information is transmitted to the radiation image detector 30, and utilized for condition setting of the signal processing described above. The radiation image detector 30 after the condition setting transmits a ready signal to the portable console device 31 to inform a ready state after preparation. Thus, a veterinarian D or operator at the portable console device 31 can find the ready state of the radiation image detector 30.

The portable console device 31 in the image browsing mode receives a radiation image from the radiation image detector 30, and drives the touchscreen display unit 31a to display the radiation image. After the image browsing, the radiation image is transmitted from the portable console device 31 to the image server 12.

The portable console device 31 in the image browsing mode is also used for photographing an optical image of the animal body P. The touchscreen display unit 31a displays a check menu option for retrieving the optical image. Also, the formed optical image of the animal body P is displayed on the touchscreen display unit 31a. For example, the optical image of the animal body P is photographed in the examination room shortly before the start of the image browsing. After obtaining the optical image, the portable console device 31 is carried by the veterinarian D or operator to the animal owner waiting outside the examination room, to show him or her the optical image of the animal body P on the portable console device 31. This, is effective in preventing misidentification of the animal of the animal body P even in presence of the other animals. The animal body P can be identified as reliably as for a human patient in the human medicine.

Also, the veterinarian D can compare and check the optical image on the portable console device 31 with the animal body P before radiographic imaging. Errors in identifying the animal body P can be prevented reliably in comparison with the use of only the body ID. Also, the optical image of the animal body P remains displayed on the same display even while the veterinarian D shows the radiation image on the portable console device 31 to the animal owner and explains the progress. Thus, the animal owner can confirm the identity of the animal body P of his or her animal in relation to the radiation image. Furthermore, the veterinarian D can check and review the progress of the animal body P, because the optical image of the animal body P is displayed even while radiation images of the past image browsing are viewed in the image viewing mode.

The optical image of the animal body P can have such a form that a portion of the animal body P with visual distinction appears in an image area of the optical image. For example, a face image of the animal body P is photographed assuming that the animal body P is distinguished by its face. A skin hair image or surface pattern image of the animal body P is photographed assuming that the animal body P is distinguished by its skin hair or surface pattern. The optical image of the animal body P is transmitted to the image server 12 together with the radiation image.

The portable console device 31 set in the image viewing mode sends a request of image distribution to the image server 12. Then the portable console device 31 receives past radiation images and past optical images from the image server 12 upon transmission of the distribution request. The radiation images and optical images being received are ready to be displayed on the touchscreen display unit 31a.

The image server 12 is a server for managing the radiation image and optical image from the portable console device 31. The image server 12 is installed in the veterinary clinic in the embodiment, but may be disposed in a data center or information center in a site separate from the veterinary clinic. The image server 12 includes a radiation image database 33 (DB) as a radiation image storage medium, and an optical image database 34 (DB) as an optical image storage medium. The radiation image database 33 stores radiation images. The optical image database stores optical images. The image server 12 writes the radiation image and optical image to respectively the image databases 33 and 34 upon receiving those from the portable console device 31. Also, the image server 12 performs search in the image databases 33 and 34 in response to a request of distribution from the portable console device 31 in the image viewing mode, and transmits the searched radiation image and optical image to the portable console device 31.

In FIG. 3, the radiation image detector 30 includes the sensor panel 37 and the housing 38 for containing the sensor panel 37. An imaging surface 38a is a front surface of the housing 38 and receives radiation. A back surface 38b is opposite to the imaging surface 38a in the housing 38. The imaging surface 38a and the back surface 38b are in a shape of a rectangular quadrilateral. A radio-transparent plate 39 is included in the housing 38 to constitute the imaging surface 38a, and transmits radiation or X-rays.

The sensor panel 37 is an indirect conversion type having a scintillator and a photoconductor (not shown). The scintillator converts radiation into visible light. The photoconductor converts the visible light into an electric signal. An example of the photoconductor is a TFT active matrix board, and has an imaging area having plural pixels arranged in a two-dimensional manner for storing charge according to dose of incident radiation. Each pixel is constituted by a photo diode and a TFT. An example of the scintillator is phosphor such as cesium iodide, and is opposed to the entire surface of the imaging area.

The housing 38 contains various elements in addition to the sensor panel 37, inclusive of a control circuit board, communication control unit, battery (not shown) and the like. The control circuit board includes a gate driver, readout circuit, A/D converter, memory and the like. The gate driver drives photoconductors in the sensor panel 37. The readout circuit reads out an image signal from the photoconductors. The A/D converter converts the read image signal into digital data of a radiation image. The memory stores the radiation image. The communication control unit has a radio communication interface for radio communication with the portable console device 31. The battery supplies the sensor panel 37 and the other elements with power. The radiation image detector 30 is a wireless type having the radio communication circuit, and can be easily handled because of unnecessity of a power cable by use of the battery.

Figure 4:
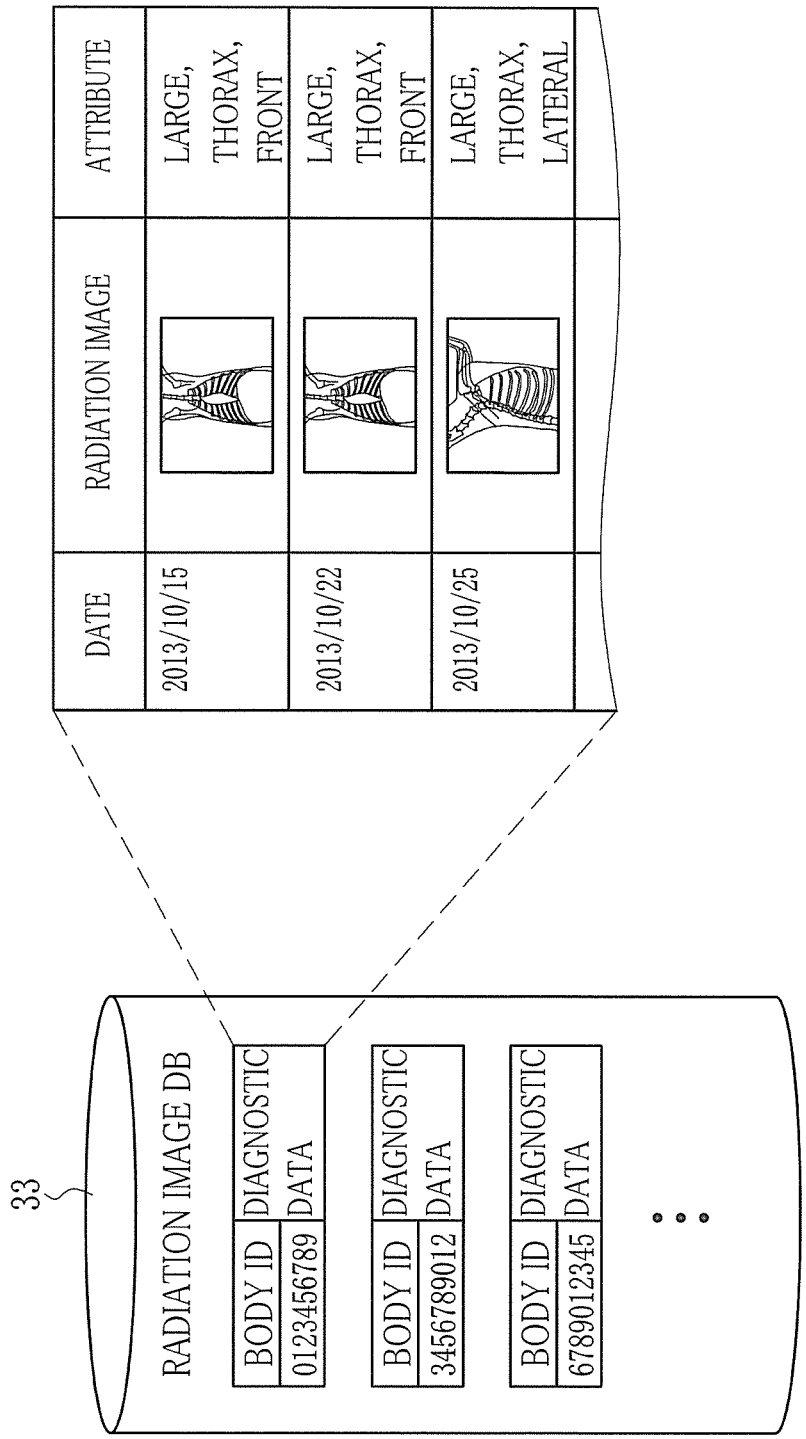
FIG. 4 is an explanatory view illustrating a radiation image database.

In FIG. 4, the radiation image database 33 stores plural diagnostic data including at least one radiation image formed by the radiographic imaging system 11. A body ID for the animal body P is assigned to the radiation image, and can be used for searching the radiation image. In the diagnostic imaging, plural radiation images may be formed by imaging the animal body for plural body parts or in plural imaging direction in one event of the imaging. A case ID is assigned to the set of the plural radiation images of the one imaging event, to manage the radiation images together. In the diagnostic data, the radiation images are managed per the date and time of the diagnostic imaging. Also, attribute information is assigned to each of the radiation images. Data in the attribute information include animal type information and imaging information determined upon registering the user menu option.

Figure 5:
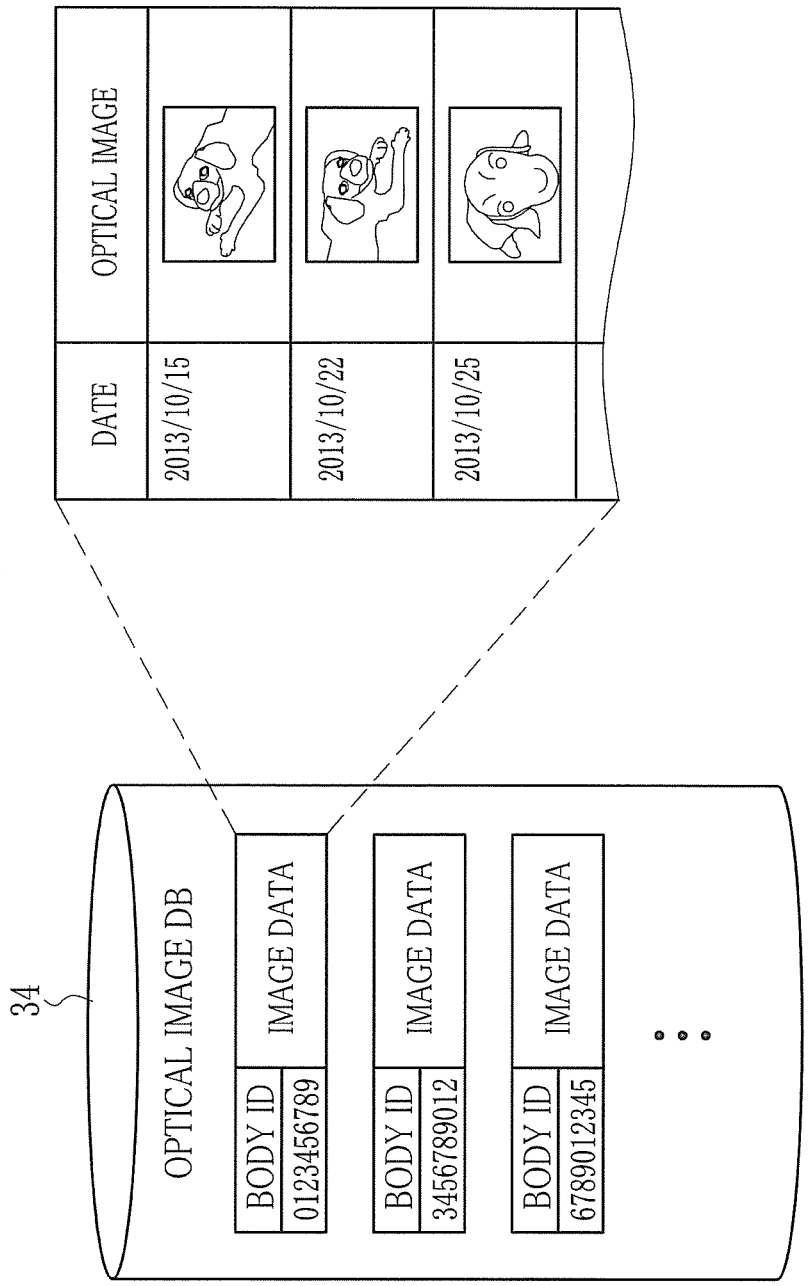
FIG. 5 is an explanatory view illustrating an optical image database.

In FIG. 5, the optical image database 34 stores body image data including optical images of the animal body P. The optical images are assigned with body IDs, with which the optical images can be searched. Assuming that it is difficult to identify the animal body P by use of the optical images, it is possible to record a plurality of optical images in one event of imaging. Also, optical images are utilized not only for identifying the animal body P but also for recording a progress note of injury, a state of skin, or the like. To this end, plural optical images may be recorded at one event of imaging. Plural optical images obtained in the imaging of one event are assigned with a single case ID and managed as optical images of one case. Also, optical images in body image data are managed for a date and time of performing the diagnostic imaging.

Figure 6:
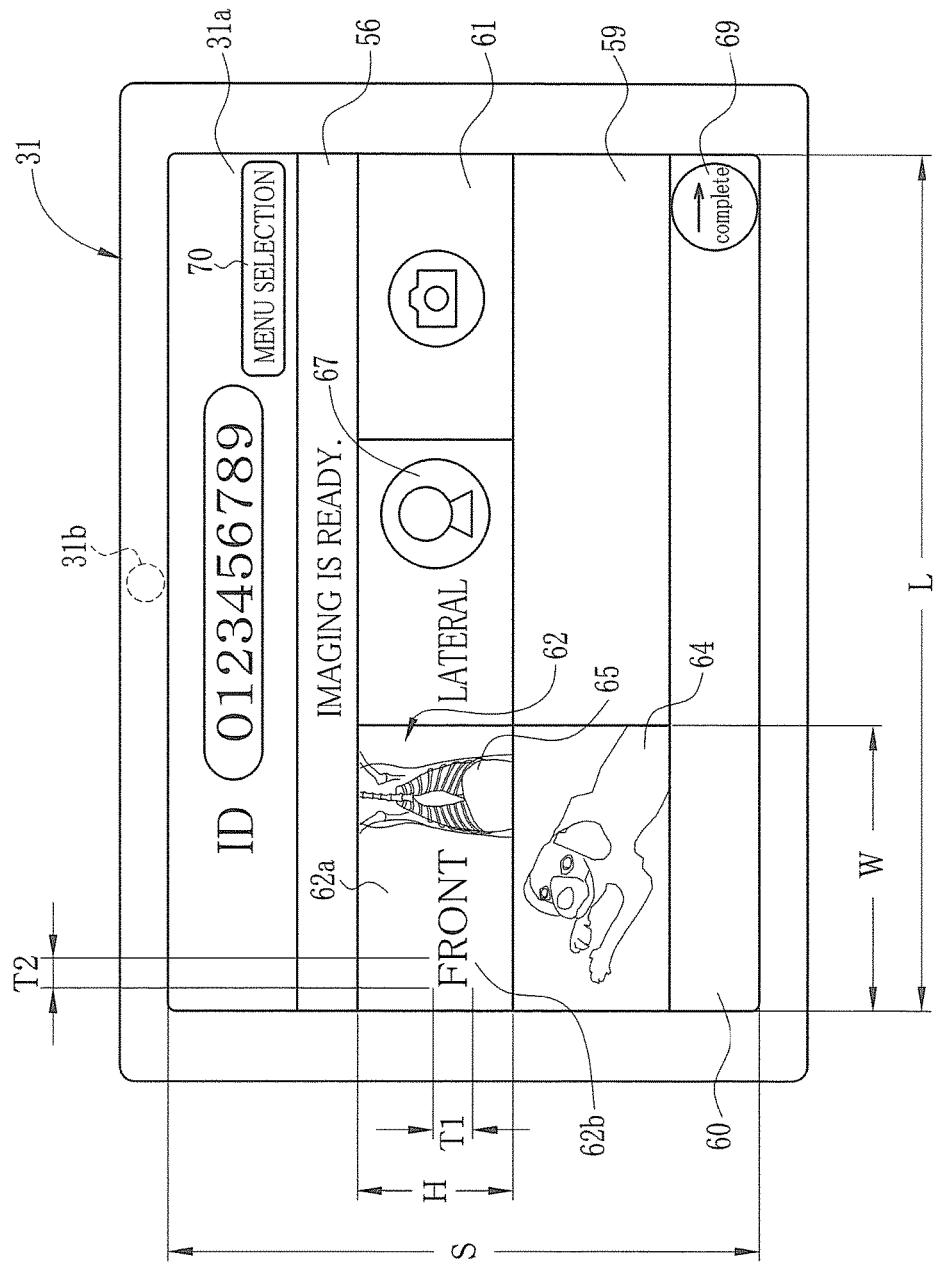
FIG. 6 is a plan illustrating a console device of a portable type.

In FIG. 6, the portable console device 31 is used in a state of horizontally extending the touchscreen display unit 31a of a quadrilateral form, or vertically extending the same. An optical camera unit 31b or optical image forming unit is disposed in a back surface of the portable console device 31 for photographing the animal body P to form an optical image. A user page 56 or browse page (input screen) is displayed on the touchscreen display unit 31a for the image browsing. The user page 56 includes a sample window area 59 or list display area, which displays a user menu option 62 or radiation image retrieving menu option, a check menu option 61 or optical image retrieving menu option, and the like in a list form. The user menu option 62 includes a display area 62a and attribute information 62b or alphanumeric information. The display area 62a extends horizontally in a form of a rectangular quadrilateral. The attribute information 62b is displayed in the display area 62a and represents the animal type information and imaging information. The display area 62a is an active input area (active touch area) to respond to manual touch.

The tablet terminal device as a basis of the portable console device 31 is a tablet terminal device of which the touchscreen display unit 31a is in a size with a length (L) equal to or less than 260 mm and a width (S) equal to or less than 180 mm, namely in a screen size of 12 inches or less. This is for the reason of easy handling in manually operating the portable console device 31 while the animal body P is set suitably, and handlability in carrying the portable console device 31 in order to show optical images or radiation images of the animal body P to its animal owner. Note that the touchscreen display unit 31a should have a sufficiently large size for the purpose of ensuring operability of the user page 56 and recognition of radiation images. The size of the touchscreen display unit 31a preferably can be equal to or more than 7 inches.

The portable console device 31 is used not only while held manually by a hand but also while placed distantly from the veterinarian D. While the portable console device 31 is placed distantly, visual recognition of the portable console device 31 to the veterinarian D may be considerably poor assuming that a size of the attribute information 62b on the touchscreen display unit 31a is small. In the portable console device 31 of the present embodiment, each of the height T1 and width T2 of the attribute information 62b in the menu are set equal to or more than 5 mm. Should the height T1 and width T2 of the attribute information 62b be too large, an area for displaying a radiation image or optical image of the animal body P will be too small. Thus, each of the height T1 and width T2 of the attribute information 62b in the menu can be preferably set equal to or less than 20 mm.

Note that the height T1 and width T2 of the attribute information 62b are determined by an experiment of recognition. The experiment of recognition was conducted. To this end, specifically, the portable console device 31 was positioned at a point distant from a human subject with a predetermined distance. Samples of the attribute information 62b with differences in the height T1 and width T2 were displayed one after anther, to measure recognition of the human subject at each one of sizes of letters in the samples. An example of the distance between the human subject and the portable console device 31 was set from a maximum distance of the portable console device 31 from a veterinarian D, for example, 1 meter. As a result of the experiment of the recognition, recognizable sizes of the attribute information 62b were found as each of the height T1 and width T2 equal to or more than 5 mm.

As the touchscreen display unit 31a of the portable console device 31 is operated by manual touch of a finger or the like, errors in operation are likely to occur assuming that an active input area of the touchscreen display unit 31a is excessively small. In the present embodiment, a height H and width W of the display area 62a or active input area in the user menu option 62 are set respectively equal to or more than 13 mm.

Figure 7:
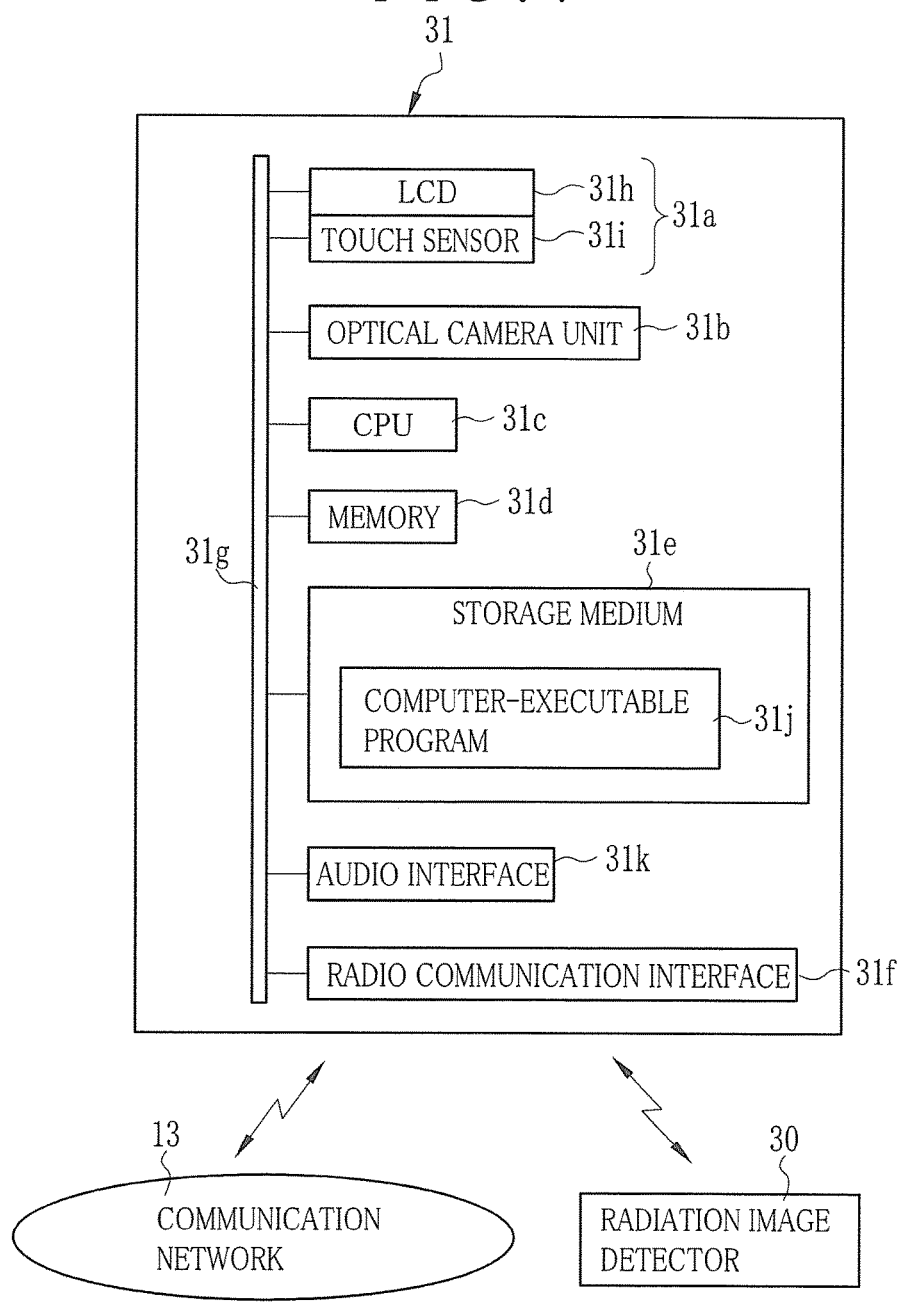
FIG. 7 is a block diagram schematically illustrating the console device.

The portable console device 31 is on the basis of a tablet terminal device having the touchscreen display unit 31a with a size equal to or less than 12 inches, and is constituted by installing a control program, such as an operating system (OS), an application program, and the like. In FIG. 7, the portable console device 31 includes the touchscreen display unit 31a, a console housing, the optical camera unit 31b, a CPU 31c, a memory 31d, a storage medium 31e or storage device, an audio interface 31k or speaker/microphone for inputs and outputs, and a radio communication interface 31f. A data bus 31g interconnects the touchscreen display unit 31a, the optical camera unit 31b, the CPU 31c, the memory 31d, the storage medium 31e, the audio interface 31k and the radio communication interface 31f.

The touchscreen display unit 31a includes a liquid crystal display panel 31h (LCD) and a touch sensor 31i for detecting touch on the liquid crystal display panel 31h. The portable console device 31 receives inputs of manual operation by detecting touch on the liquid crystal display panel 31h with the touch sensor 31i. The optical camera unit 31b is previously incorporated in the tablet terminal device as a basis, and includes a taking lens and an image sensor (not shown) for forming an image focused by the taking lens.

The storage medium 31e is a device for storing various data, for example, a non-volatile memory. The storage medium 31e stores the control program (not shown) described above, and a computer-executable program 31j or portable console program. The computer-executable program 31j is an application program for the tablet terminal device to function as the portable console device 31. Also, the storage medium 31e stores radiation images received from the radiation image detector 30 or the image server 12, and optical images acquired by the optical camera unit 31b.

The memory 31d is a working memory with which the CPU 31c performs tasks. The CPU 31c loads the memory 31d with the control program and the computer-executable program 31j read from the storage medium 31e, and controls various elements in the tablet terminal device by running the programs and performing the tasks. The audio interface 31k for inputs and outputs processes input and output audio data. To output audio data, a speaker (not shown) is used to output sound or voice. The radio communication interface 31f is an interface for wireless connection to the communication network 13 and to the radiation image detector 30.

Figure 8:
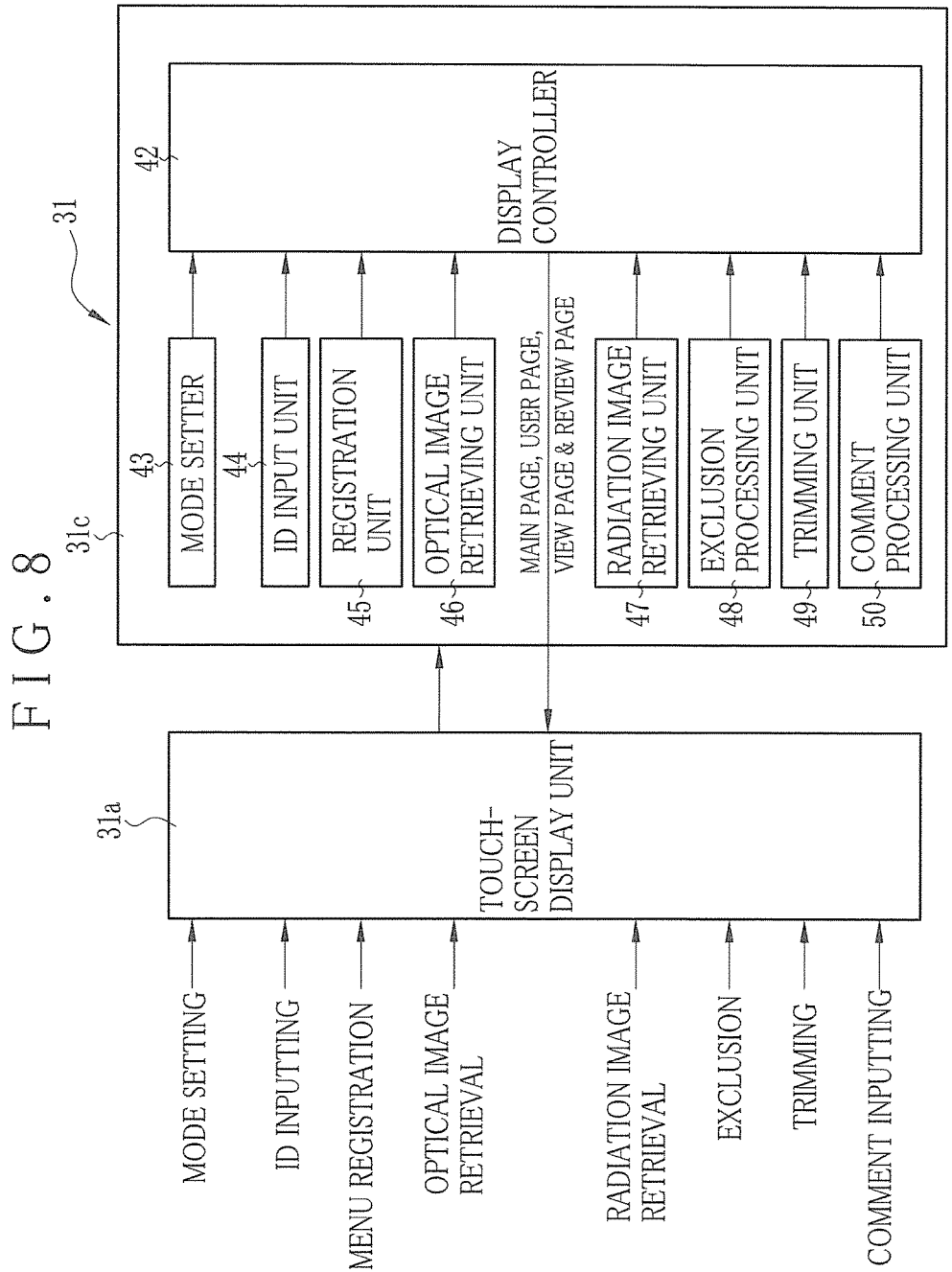
FIG. 8 is a block diagram schematically illustrating circuit devices in a CPU in the console device.

In FIG. 8, the CPU 31c is caused to have various elements upon running the computer-executable program 31j in the portable console device 31, the various elements including a display controller 42, a mode setter 43, an ID input unit 44, a registration unit 45 or selection unit, an optical image retrieving unit 46 or optical image acquisition unit, a radiation image retrieving unit 47 or radiation image acquisition unit, an exclusion processing unit 48 or turn-off processing unit, a trimming unit 49 and a comment processing unit 50. The display controller 42 in response to operation of the portable console device 31 creates various pages (screen views) inclusive of a main page or mode setting page (home screen), the user page 56, a view page or image page (viewer screen), and the like, which are displayed on the touchscreen display unit 31a. The mode setter 43 sets one of an image browsing mode and image viewing mode for an operation mode in response to the mode setting detected by the touchscreen display unit 31a.

The ID input unit 44 performs processing of ID reception to receive the body ID for the animal body P in response to an input of ID detected by the touchscreen display unit 31a. The registration unit 45 processes menu registration to register the user menu option according to an input of the menu registration detected by the touchscreen display unit 31a. The optical image retrieving unit 46 performs processing of optical image retrieval to retrieve the radiation image of the animal body P according to an input of the optical image retrieval detected by the touchscreen display unit 31a. The radiation image retrieving unit 47 performs processing of radiation image retrieval to retrieve the radiation image according to an input of the radiation image retrieval detected by the touchscreen display unit 31a.

The exclusion processing unit 48 responds to a command signal of image exclusion detected by the touchscreen display unit 31a, and performs image exclusion to set a formed radiation image as an excluded image without use for image browsing. The trimming unit 49 responds to a command signal of trimming detected by the touchscreen display unit 31a, and performs trimming to extract a predetermined area within the radiation image. The comment processing unit 50 responds to a command signal of comment detected by the touchscreen display unit 31a, and performs comment processing to add the comment to the radiation image.

Figure 9:
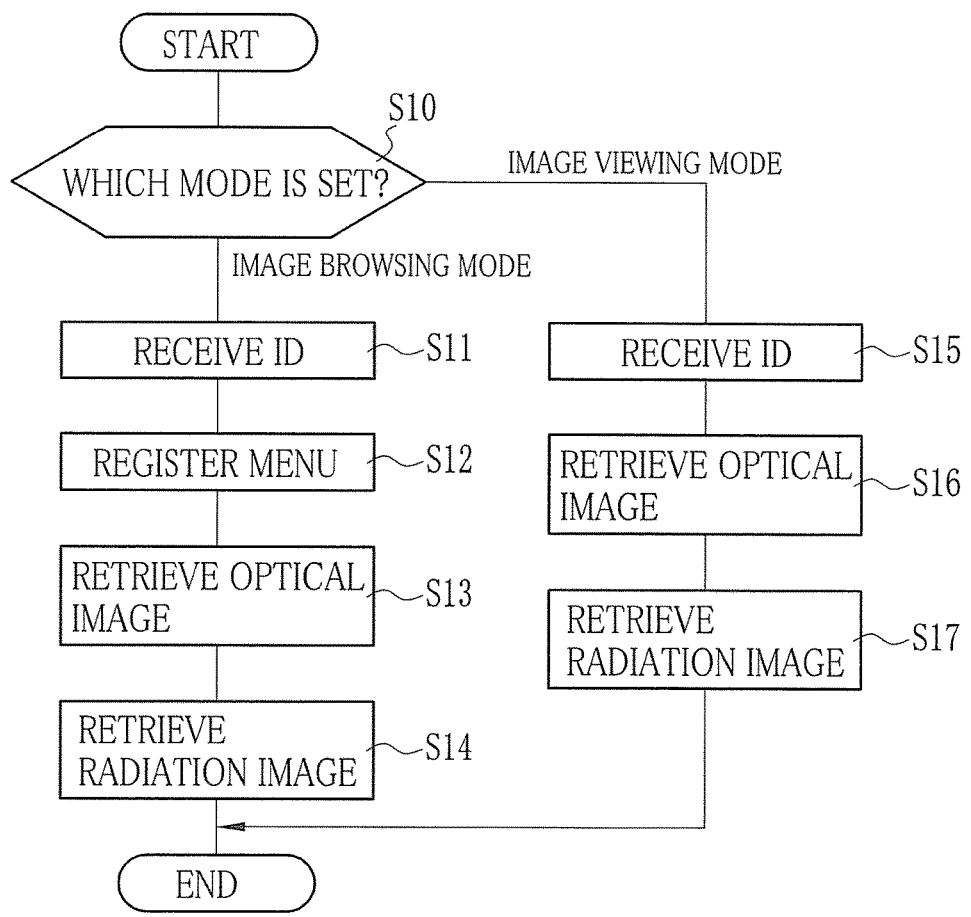
FIG. 9 is a flow chart illustrating a flow of operation in the console device.

In FIG. 9, the portable console device 31 performs a task of the mode setting (S10) for setting an operation mode. In case the image browsing mode is set in the mode setting, the ID reception (S11), the menu registration (S12), the optical image retrieval (S13) and the radiation image retrieval (S14) are performed sequentially. In the ID reception, the body ID is received. In the menu registration, a user menu option for radiation image retrieval is registered. In the optical image retrieval, an optical image of the animal body P is retrieved. In the radiation image retrieval, a radiation image of the animal body P is retrieved. The display controller 42 processes the display screen according to results of the tasks, and drives the touchscreen display unit 31a to display the display screen. Note that the menu registration (S12) may be performed after the optical image retrieval (S13) according to a sequence of manual input of the veterinarian D. In case the image viewing mode is set in the mode setting, the ID reception (S15), and the radiation image retrieval (S16) and the optical image retrieval (S17) from the image server 12 can be performed in this sequence. Each of those steps includes display processing for driving the touchscreen display unit 31a to display one of various items, such as the received body ID, the registered user menu option, and the retrieved optical image or radiation image.

Figure 10:
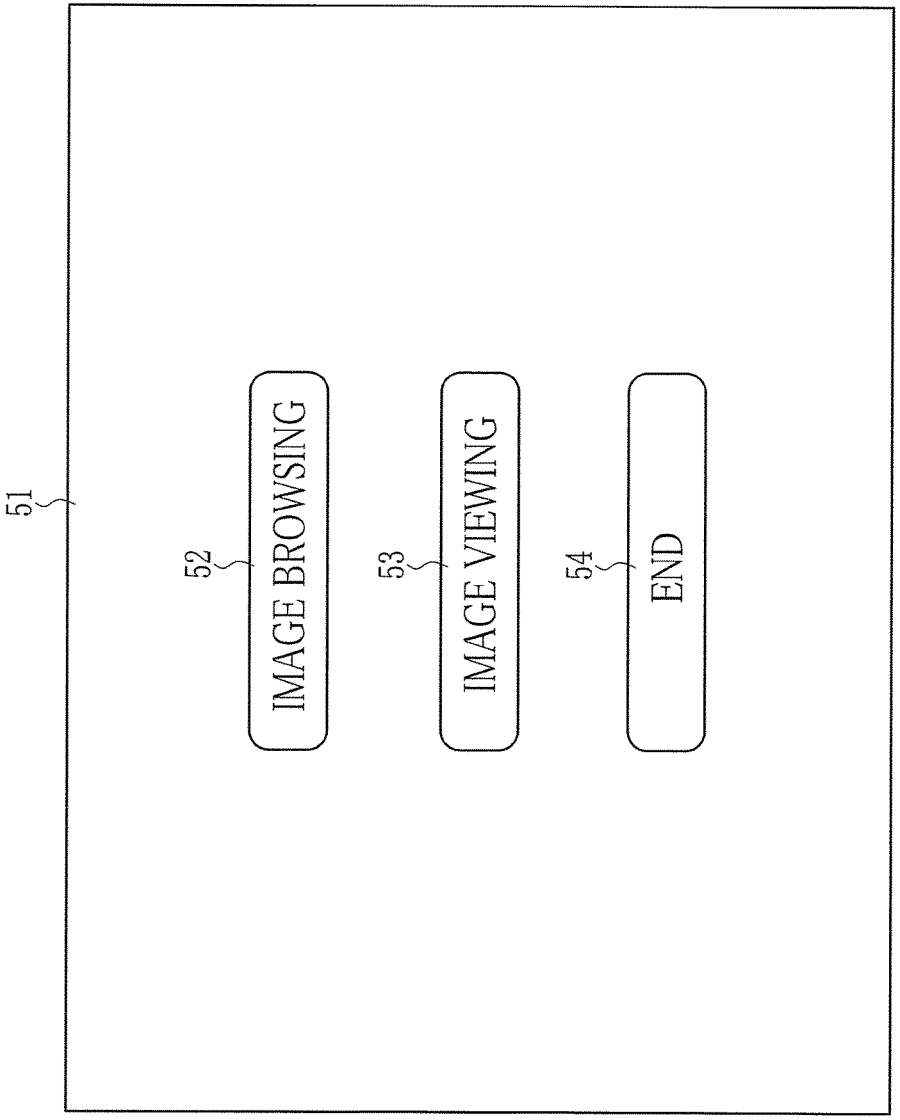
FIG. 10 is a plan illustrating a main page in the console device.

In FIG. 10, a main page 51 or mode setting screen is displayed on the touchscreen display unit 31a by the display controller 42 in a mode setting step in a form of GUI (graphical user interface) for manual operation. A veterinarian D or operator touches the touchscreen display unit 31a with fingers or the like to operate the main page 51 and other screen view. The main page 51 includes an image browsing button 52, an image viewing button 53 and an end button 54. The image browsing button 52 changes over the portable console device 31 to the image browsing mode. The image viewing button 53 changes over the portable console device 31 to the image viewing mode. The end button 54 terminates the computer-executable program 31j. The mode setter 43 sets the operation mode of the portable console device 31 according to mode setting of the main page 51.

Figure 11:
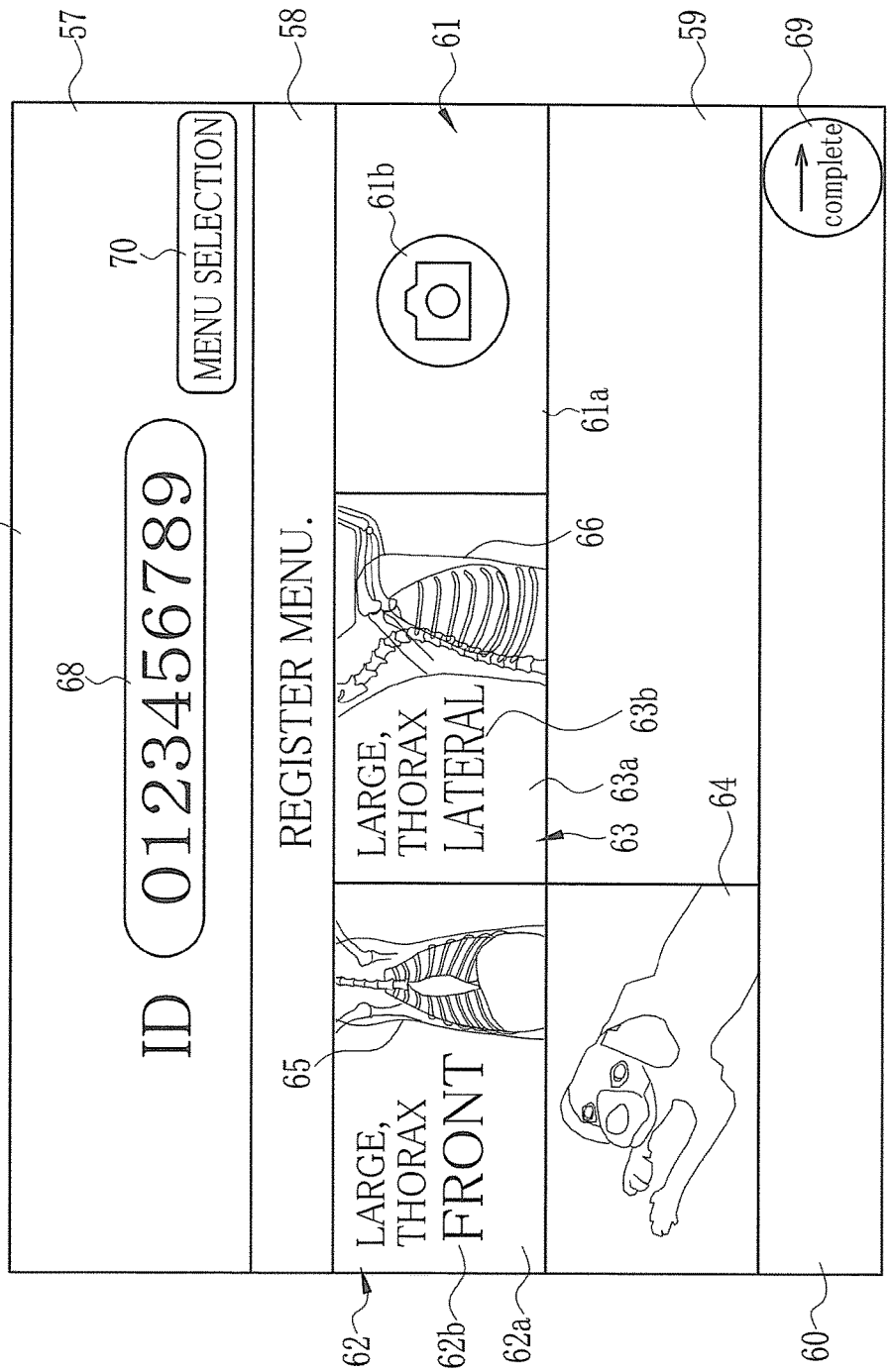
FIG. 11 is a plan illustrating a user page.

Changing over the portable console device 31 to the image browsing mode by use of the image browsing button 52 changes over the touchscreen display unit 31a from the main page 51 to the user page 56 for the image browsing as illustrated in FIG. 11. The user page 56 includes an ID input area 57, a status display area 58, the sample window area 59 and an end button area 60 in a downward sequence in the drawing.

An ID input field 68 is disposed in the ID input area 57 for inputting ID information. The ID input field 68 upon being touched is changed over for a state of receiving an input of the body ID. A cursor movable together with alphanumeric information of input letters is indicated in the ID input field 68. Also, a software keyboard (not shown) is displayed in a lower portion of the user page 56 for inputting the body ID, for example, in a portion overlapping with the sample window area 59. In case a body ID with alphanumeric information of letters of a predetermined number is input, the ID input field 68 is changed over from a receiving state to an indication state, and indicates the input body ID. The ID input unit 44 for processing ID reception receives the body ID input by the ID input field 68.

In a veterinary clinic having an electronic medical chart system, the radiography system architecture 10 is connected to the electronic medical chart system so that a body ID can be acquired from the electronic medical chart system. However, an ordinary type of veterinary clinic uses medical charts of paper documents for recording and managing diagnostic information of an animal body P without introducing an electronic medical chart system. Thus, the ID input field 68 is provided in the present embodiment for manually inputting body IDs for use in an ordinary veterinary clinic without having an electronic medical chart system. Note that manual operation for inputting body IDs is likely to be wrong incidentally with human operation. However, the ID input field 68 in the user page 56 displays an input body ID continuously, so that a veterinarian can be aware of his or her error upon incidental occurrence after a body ID is input. Also, an optical image according to the input body ID is displayed in the user page 56. Errors in inputting a body ID can be discovered easily, because the optical image can be used for a confirmation image for the body ID.

The status display area 58 displays a message according to a status of the sample window area 59. For example, the status display area 58 displays a message of "REGISTER MENU" (select) assuming that the user menu option is not registered in the sample window area 59, or assuming that imaging of radiation images according to the user menu option registered in the sample window area 59 has been completed. Also, the status display area 58 displays a message of "IMAGING IS READY" assuming that the user menu option before imaging is displayed in the sample window area 59 and assuming that a ready signal according to the user menu option is received from the radiation image detector 30.

The sample window area 59 displays the check menu option 61, the user menu option 62 and a user menu option 63 or radiation image retrieving menu option in a list form, the check menu option 61 being for retrieval of an optical image of the animal body P. Also, the sample window area 59 displays an optical image 64 (identification image) of the animal body P retrieved by use of the check menu option 61, and radiation images 65 and 66 of the animal body P retrieved by use of the user menu options 62 and 63. Only the check menu option 61 becomes displayed in the sample window area 59 immediately after changeover to the image browsing mode. The user menu options 62 and 63 are displayed in the sample window area 59 in the progress of the menu registration. The optical image 64 and the radiation images 65 and 66 are additionally displayed in the sample window area 59 in the progress of the optical image retrieval and radiation image retrieval.

Consequently, it is possible at one glance for the veterinarian D to recognize the progress of the image browsing inclusive of completed steps, in combined appearance of the check menu option 61, the user menu options 62 and 63, the optical image 64 and the radiation images 65 and 66. Also, the check menu option 61 and the user menu option 62 or 63 can be manually operated to start succeeding tasks immediately after recognizing the progress of the image browsing. Operability can be considerably increased by combining displayed forms of the images for the progress of the image browsing and the menu options in the same user page.

The check menu option 61 includes a display area 61a and an indicator icon 61b. The display area 61a is in a rectangular quadrilateral form and horizontally long. The indicator icon 61b is displayed within the display area 61a. The display area 61a is an active input area (active touch area) to respond to manual touch in the check menu option 61. A form of the indicator icon 61b is a figure in which optical imaging is symbolized. In the example depicted in FIG. 6, the indicator icon 61b is in a symbolized form of a camera. Note that the "OPTICAL IMAGE RETRIEVING MENU" or other alphanumeric information can be displayed in the display area 61a instead of the indicator icon 61b.

Optical image retrieval is started in response to operating the check menu option 61. The display controller 42 changes over the touchscreen display unit 31a from the user page 56 to a live camera view (live image view, not shown) for photographing an optical image of the animal body P. The optical camera unit 31b is started up by the optical image retrieving unit 46 to start photographing a live image of the animal body P. The live camera view displays the live image (live camera view) of the animal body P photographed by the optical camera unit 31b. The live image is an image or moving image on the display before depressing a shutter button for photographing so as to check an angle of photography or object to be photographed, without recording to a recording medium or the like. The live image as moving image is displayed in the live camera view.

A shutter button is disposed in the live camera view for taking an optical image of the animal body P. In case the shutter button is depressed in the live camera view, the optical camera unit 31b starts photographing the optical image of the animal body P. The display controller 42 changes over the touchscreen display unit 31a from the live camera view to the user page 56. Also, the display controller 42 creates the optical image 64 in a smaller size from the optical image. The optical image 64 of a reduced size is displayed in the sample window area 59 in such a manner that at least one portion of the animal body P with visual distinction is not overlapped with the check menu option 61. Thus, the check menu option 61 and the like can be displayed in the sample window area 59 with improved recognition by reduction of the display size of the optical image 64 in the sample window area 59. In FIG. 6, the sample window area 59 has a sufficient space. The optical image 64 is displayed in the same size as the check menu option 61 without overlap with the check menu option 61.

The user menu options 62 and 63 respectively have the display area 62a and a display area 63a extending in a horizontally longitudinal quadrilateral form. Also, the display areas 62a and 63a are active touch areas (active input areas) in the user menu options 62 and 63. The attribute information 62b and attribute information 63b or alphanumeric information is indicated in the display areas 62a and 63a for expressing the selected animal type, body part and imaging direction set upon the registration. In FIG. 6, an imaging icon 67 or indicator icon is displayed in one of the user menu options 62 and 63 in which a radiation image will be formed next. In the example depicted in the drawing, an example of the imaging icon 67 is in a symbolized form of a radiation source.

The display controller 42, upon receiving a radiation image from the radiation image detector 30 according to the user menu options 62 and 63, the radiation images 65 and 66 of a reduced size are produced from the received radiation image. The radiation images 65 and 66 are displayed in an at least partially overlapped manner with the user menu options 62 and 63. Thus, a display size of the radiation images 65 and 66 in the sample window area 59 is reduced. The user menu option 62 and the like can be displayed in the sample window area 59 with improved recognition. In FIG. 6, the display areas 62a and 63a have a sufficient space in the user menu options 62 and 63, so the radiation images 65 and 66 being displayed are contained in the display areas 62a and 63a.

In the end button area 60, an end button 69 is displayed for indicating an end of the image browsing. Upon completion of imaging of radiation images in relation to the user menu options 62 and 63 displayed in the sample window area 59, the end button 69 becomes displayed in the end button area 60. Depression of the end button 69 causes the portable console device 31 to transmit radiation images of the animal body P from the radiation image detector 30 and formed optical images to the image server 12. Also, the portable console device 31 ends the image browsing mode and returns to the mode setting. The touchscreen display unit 31a displays the main page 51 of FIG. 10.

A selection button 70 or menu registration button in the ID input area 57 is used for menu registration. In FIG. 12, an animal type list 72 is displayed upon operating the selection button 70 in a selectable manner and in a state overlapped with the user page 56. Examples of information in the animal type list 72 are "LARGE" for a large dog or the like, "MEDIUM" for a medium size dog or the like, and "SMALL" for a small dog, cat or the like. In case any one of the types of the animals is selected in the animal type list 72, a body part list 73 is displayed in a selectable manner in place of the animal type list 72. The body part list 73 indicates examples of body parts in a list form, inclusive of "THORAX", "ABDOMEN" and "HEAD".

In case any one of the body parts is selected in the body part list 73, an imaging direction list 74 is displayed in a selectable manner in place of the body part list 73. The imaging direction list 74 indicates examples of imaging directions in a list form, inclusive of "FRONT", "LATERAL" and "DIAGONAL". In the example in FIG. 12, the options of "LARGE", "THORAX" and "FRONT" are selected in the animal type list 72, the body part list 73 and the imaging direction list 74. Color of selected background portions of the animal type list 72, the body part list 73 and the imaging direction list 74 is changed, to clarify the selected background portion to the veterinarian D.

Upon selecting one of imaging directions from the imaging direction list 74, the user menu option 62 or 63 according to the selected animal type, body part and imaging direction is registered in the portable console device 31. Note that the menu registration can be performed in a method other than described above. It is possible to register a menu option by operating the selection button 70 in one of various screen views after opening the screen view upon touching one of various setting buttons (not shown) disposed in the ID input area 57.

In FIG. 11, the selected animal type, body part and imaging direction are added to the registered user menu option 62 or 63 as animal type information and imaging information. The user menu options 62 and 63 being registered are displayed in the sample window area 59 in a manner visible simultaneously, as described heretofore. The attribute information 62*b* and 63*b* expresses the selected animal type, body part and imaging direction set upon the registration. For example, the user menu option 62 is registered according to the animal type list 72, the body part list 73 and the imaging direction list 74 in FIG. 12. Letters of "LARGE", "THORAX" and "FRONT" are displayed in the display area 62*a* according to the animal type, body part and imaging direction set at the time of the registration.

In the processing of the radiation image retrieval, the portable console device 31 transmits animal type information and imaging information to the radiation image detector 30 according to a sequence of registering the user menu options 62 and 63. In case condition setting of the signal processing is terminated in the radiation image detector 30 according to the animal type information and imaging information, the portable console device 31 receives a ready signal from the radiation image detector 30. The display controller 42 upon receiving the ready signal causes the status display area 58 to display a message of "IMAGING IS READY".

Radiographic imaging is performed according to the sequence of the registration of the user menu options 62 and 63. However, a sequence of the imaging can be changed by selecting the user menu option 62 or 63 on the user page 56. For example, the user menu option 63 is selected by a touch while the imaging with the user menu option 62 is ready. The imaging icon 67 in the user menu option 62 is deleted. The imaging icon 67 is displayed in the user menu option 63 instead. Also, the animal type information and imaging information of the user menu option 63 is transmitted to the radiation image detector 30, to perform condition setting of signal processing prior to the imaging.

The number of the user menu options 62 and 63 registered in the portable console device 31 is not limited to two. One or three or more of the user menu options can be registered, for example, according to the number of plural radiation images created at one event of the image browsing. Assuming that the sample window area 59 cannot display all of the plural user menu options simultaneously, then the sample window area 59 is set in a scrollable form, for a user to view all of the plural user menu options by scrolling.

Figure 13:
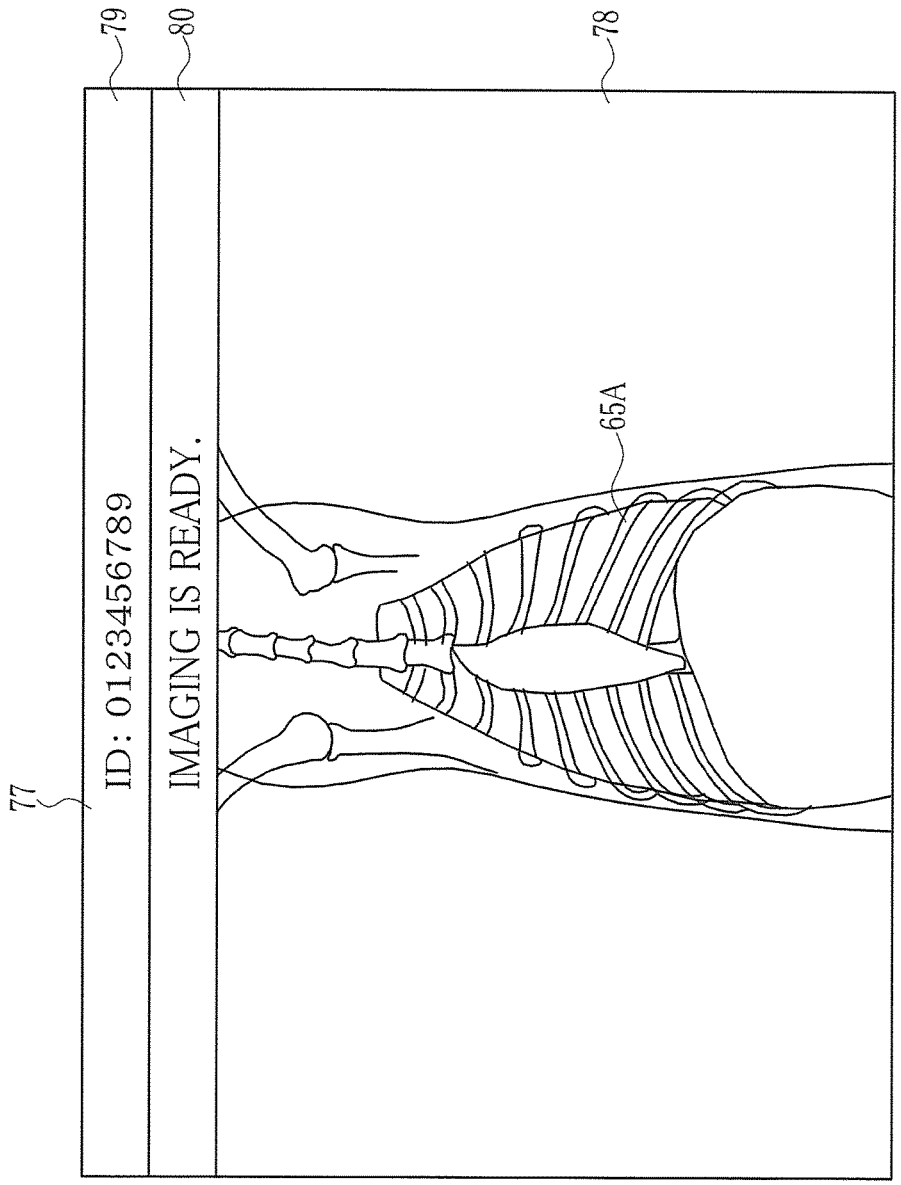
FIG. 13 is a plan illustrating a view page with a radiation image.

In case the user menu option 62 or 63 in the user page 56 is touched continuously at least for a predetermined period, namely, by long press, then the display controller 42 changes over the touchscreen display unit 31*a* from the user page 56 to a view page 77 or image screen as illustrated in FIG. 13. Also, upon receiving the radiation image from the radiation image detector 30, the view page 77 is changed over from the user page 56. The view page 77 is used for retrieval of radiation images and aid in explaining radiation images to an animal owner, and includes an image display area 78 for a radiation image, and window areas 79 and 80 disposed higher than the image display area 78 for indicating a body ID and status information. Assuming that the user menu option 62 or 63 before imaging is touched by long press for changeover to the view page 77, the image display area 78 does not display any item. However, assuming that a radiation image is received, or assuming that the user menu option 62 or 63 after imaging is touched by long press, then the image display area 78 displays a received radiation image 65A.

Figure 14:
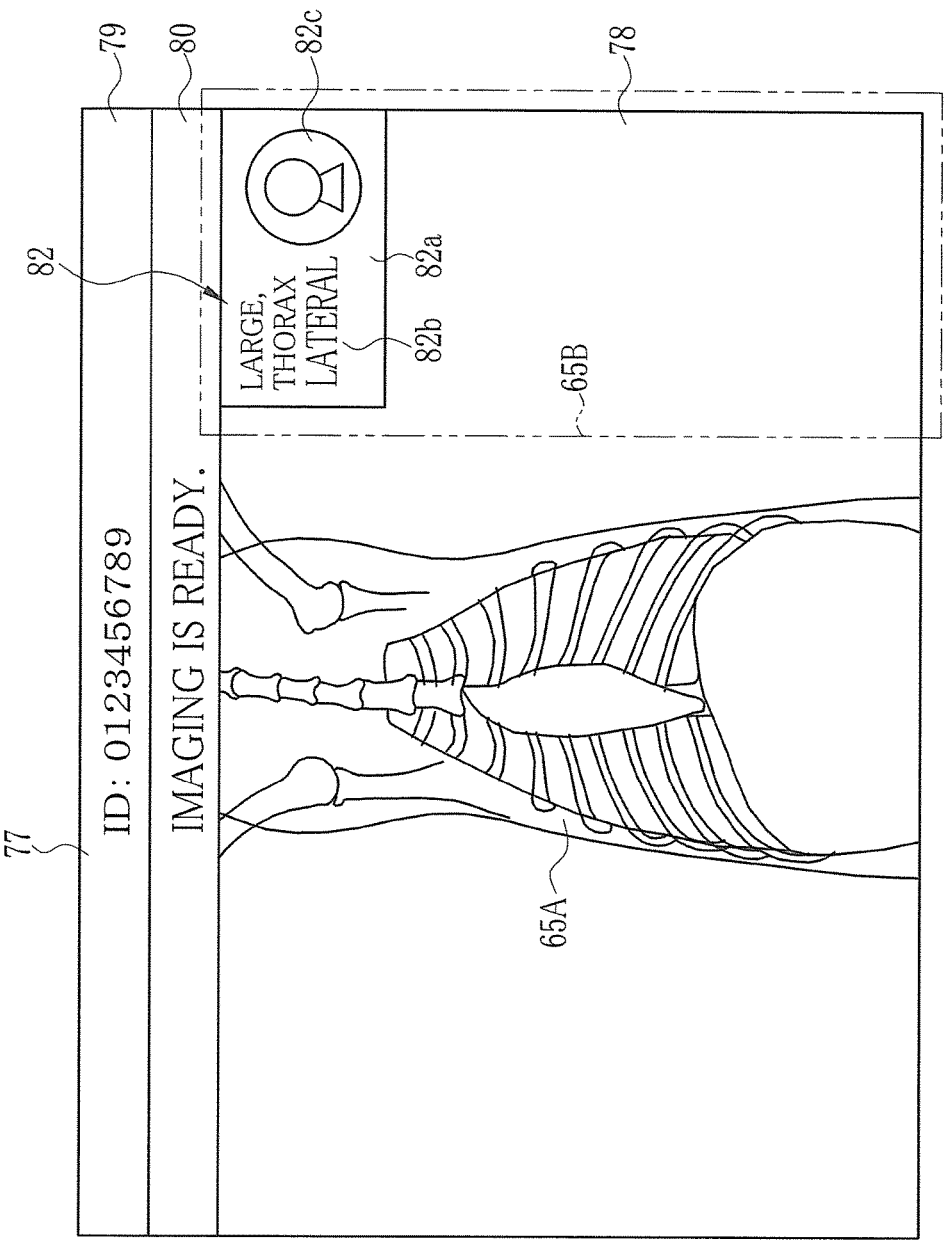
FIG. 14 is a plan illustrating the view page with the radiation image and a succeeding user menu option.

Also, the display controller 42 performs display processing of a succeeding user menu option among plural user menu options in the image display area 78 upon lapse of predetermined waiting time of display after the radiation image 65A becomes displayed on the image display area 78. The succeeding user menu option is a menu related to a succeeding radiation image next to the radiation image 65A currently displayed in the image display area 78. In FIG. 14, a succeeding user menu option 82 or second radiation image retrieving menu option includes a frame line 82*a*, attribute information 82*b* or alphanumeric information, and an imaging icon 82*c* or indicator icon. The frame line 82*a* divides the display area. The attribute information 82*b* represents an animal type, body part and imaging direction of a succeeding radiation image. Note that the imaging icon 82*c* may be omitted. Graphic representations of any type can be used for expressing an animal type, body part and imaging direction for the purpose of visual information. Also, the waiting time may be not predetermined, but can be changeable in a dynamically changing manner.

The succeeding user menu option 82 is displayed in an overlapped manner with a blank margin portion of the radiation image 65A. The blank margin portion is a pass-through area 65B where radiation is directly detected by the radiation image detector 30. In FIG. 14, the radiation image 65A is displayed in the image display area 78 after imaging according to the user menu option 62. In the succeeding user menu option 82, menu items corresponding to the user menu option 63 are displayed. The succeeding user menu option 82 is disposed in an upper right portion of the radiation image 65A.

Figure 15:
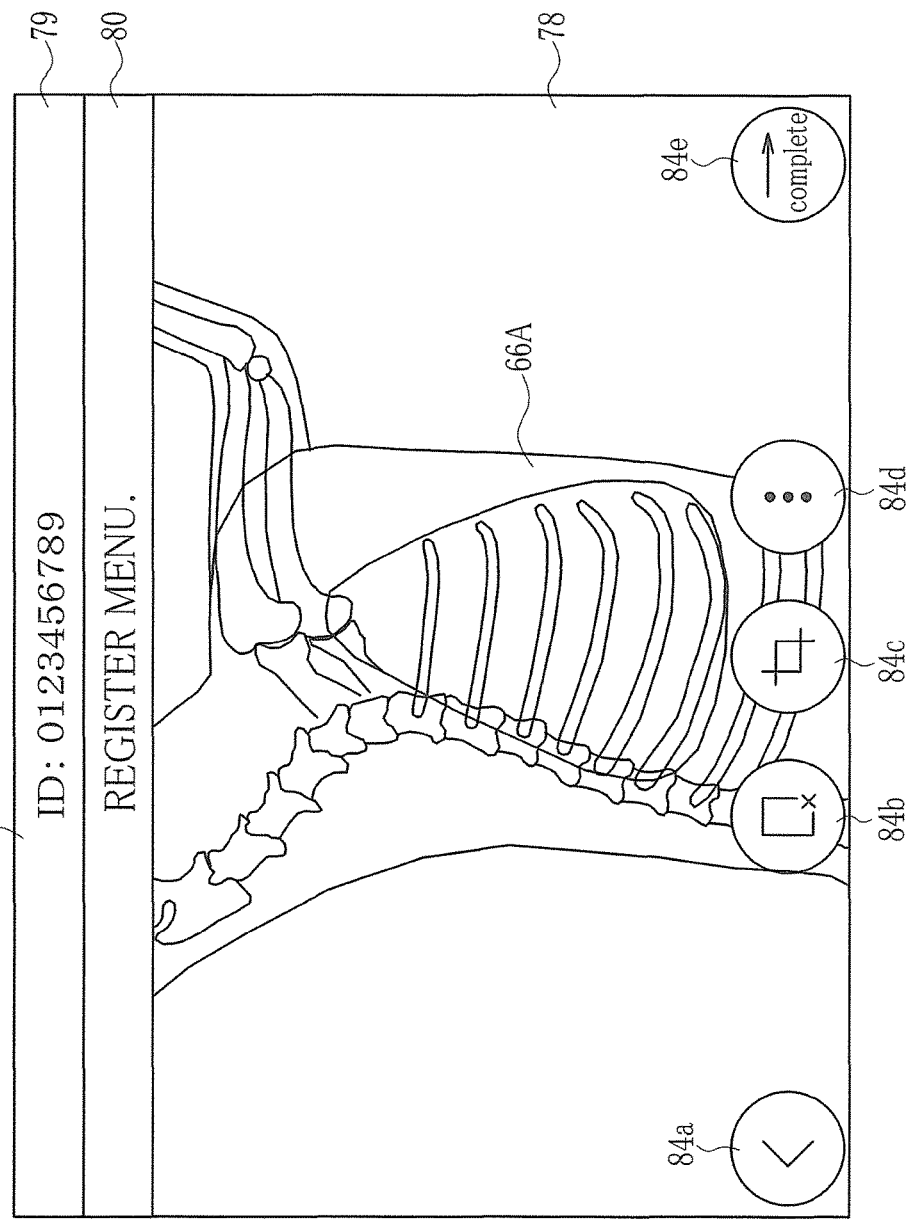
FIG. 15 is a plan illustrating the view page with operation buttons.

Upon imaging according to the succeeding user menu option 82, the image display area 78 displays a radiation image 66A formed according to the succeeding user menu option 82 as illustrated in FIG. 15. Note that the imaging of the succeeding user menu option 82 can be performed while the view page 77 is displayed or after changeover from the view page 77 to the user page 56. However, it is preferable to perform the imaging with the view page 77 assuming that imaging of plural radiation images is desired from a position distant from the veterinarian D or operator and with changes in the posture of the animal body P between events of imaging. It is possible by use of the view page 77 to check the radiation image even from a distant position, as the radiation image becomes displayed in a large size. Also, a succeeding radiation image can be previewed without leaving hands from the animal body P, because the succeeding user menu option 82 is displayed in the view page 77. Consecutive imaging is possible without manually touching the portable console device 31.

In case a flicking action on the image display area 78 is performed by touch of a finger moving quickly, the display controller 42 changes over the radiation image on the image display area 78. For example, upon flicking on the image display area 78 to a left side, a past radiation image acquired formerly before the displayed present radiation image is displayed in the image display area 78. Also, upon flicking on the image display area 78 to a right side, a new radiation image acquired after the displayed radiation image is displayed in the image display area 78.

Also, performing a flicking action to the succeeding user menu option 82 can change a sequence of imaging of radiation images by changing over user menus in the image display area 78. For example, the succeeding user menu option 82 can be flicked while imaging of the succeeding user menu option 82 is set ready. Then the succeeding user menu option 82 is deleted. Still another user menu option for planned subsequent imaging is displayed as a new user menu option in an overlapped manner with the radiation image 65A.

Upon occurrence of an action of pinch-in of decreasing a distance between two fingers touching the image display area 78, or action of pinch-out of increasing the distance between two fingers touching the image display area 78, the display controller 42 performs display processing of reduction or enlargement of a displayed radiation image. Upon occurrence of an action of swiping of horizontally shifting a finger touching the image display area 78 or an action of swiping of vertically shifting a finger touching the image display area 78, the display controller 42 performs display processing of adjusting density or contrast of a displayed radiation image. For example, the density is adjusted upon swiping action in a vertical direction, and the contrast is adjusted upon swiping action in a horizontal direction. Note that those types of the swiping action can be allocated to the adjustment in the opposite manner.

Upon touching the image display area 78 in the view page 77, various buttons become displayed under the image display area 78, including a changeover button 84a, an exclusion button 84b or turn-off button, a trimming button 84c, a comment button 84d and an end button 84e. The changeover button 84a is operated to change over the view page 77 to the user page 56. Upon operating the changeover button 84a, the display controller 42 changes over the touchscreen display unit 31a from the view page 77 to the user page 56.

The exclusion button 84b is used for setting a radiation image as an excluded image without use for image browsing. Upon operating the exclusion button 84b, a radiation image displayed in the image display area 78 is set as an excluded image. In the user page 56 in FIG. 16, two diagonal lines 63d (cancel lines) are displayed in the user menu option 63 for the radiation image set as the excluded image for recognition as the excluded image. A user menu option 86 or radiation image retrieving menu option for re-imaging is automatically registered with the same animal type information and imaging information as the excluded image, and is displayed in the sample window area 59. The animal type information and imaging information of the user menu option 86 is transmitted from the portable console device 31 to the radiation image detector 30, so that re-imaging of the excluded image can be performed easily.

The trimming button 84c is used for trimming of a radiation image. Upon depressing the trimming button 84c, a quadrilateral trimming frame (not shown) is indicated in the image display area 78. A position and size of the trimming frame is adjusted, to input a command signal for trimming, so that information of a partial image in the trimming frame is stored. The comment button 84d is used for adding comment to the radiation image. Upon depressing the comment button 84d, a comment screen view and a software keyboard are displayed to overlap with the view page 77, the software keyboard being for inputting comment into the comment screen view. The input comment in the comment screen view is recorded as metadata of the radiation image. The end button 84e is used for instructing termination of image browsing in a manner similar to the end button 69 described above. Upon depressing the end button 84e, the portable console device 31 transmits the radiation image and optical images of the animal body P to the image server 12, and stores the same in the image server 12. In the user page 56, the body ID is deleted, to enable image browsing of next animal body.

Upon selecting the image viewing mode in the main page 51, receiving the ID is processed in the same manner as the image browsing mode. Then the optical image retrieving unit 46 and the radiation image retrieving unit 47 retrieve a radiation image and optical image from the image server 12 in correspondence with the body ID. The display controller 42 displays a review page (not shown) or tracking page on the touchscreen display unit 31a substantially in the same form as the user page 56. In the review page, the optical image is displayed without overlapping with the check menu option (optical image retrieving menu option). The radiation image is displayed with at least one portion overlapped with the user menu option. Upon selection of the radiation image in the review page, the touchscreen display unit 31a is changed over from the review page to a view page (not shown) substantially in the same form as the view page 77. The selected radiation image is displayed in a large size. Thus, past radiation images can be viewed.

Figure 17:
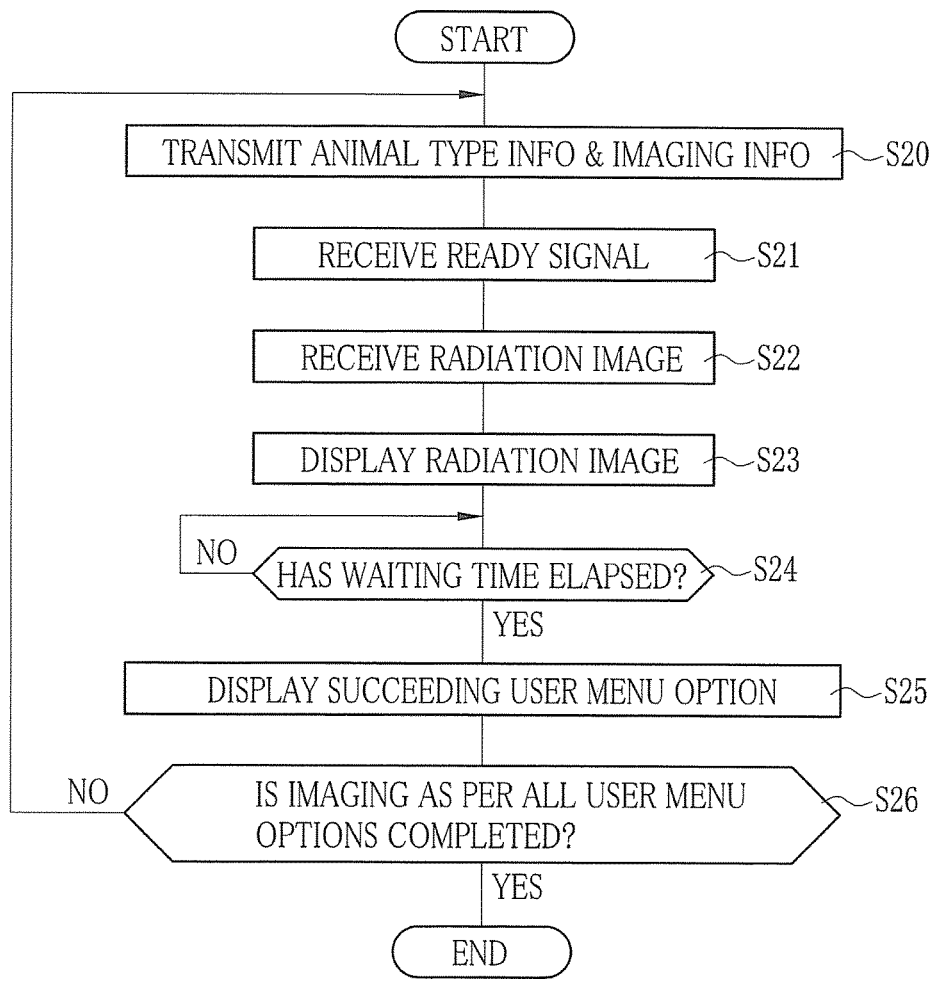
FIG. 17 is a flow chart illustrating radiation image retrieval.

A flow chart in FIG. 17 is referred to now to describe radiation image retrieval. The radiation image retrieving unit 47 transmits the animal type information and imaging information to the radiation image detector 30 in a sequence of registration or a changed sequence of imaging in the step S20, the animal type information and imaging information being registered in the sample window area 59 for a plurality of the user menu options 62 and 63. The radiation image detector 30 sets a condition of signal processing according to the animal type information and imaging information received from the portable console device 31 and the imaging condition received from the source driver 25, and transmits a ready signal to the portable console device 31 after the condition setting. The display controller 42 upon receiving the ready signal in the step S21 causes the user page 56 to display a message "IMAGING IS READY" in the status display area 58.

The radiation source 24 emits radiation to the animal body P upon turning on the radiation switch 26 by the veterinarian D. The radiation image detector 30 detects a radiation image. The radiation image detector 30 transmits the radiation image to the portable console device 31. The display controller 42 upon receiving the radiation image in the step S22, changes over the user page 56 to the view page 77, for the image display area 78 to display the received radiation image in the step S23. See FIG. 13.

After the radiation image becomes displayed in the image display area 78, the display controller 42 measures elapsed time from a start of the display, and checks whether predetermined waiting time for display has elapsed or not in the step S24. Assuming that the waiting time has elapsed (yes in the step S24), then the display controller 42 performs display processing to display the succeeding user menu option 82 in an overlapped manner with the radiation image 65A in the image display area 78, in the step S25 as illustrated in FIG. 14. Then the step for displaying the succeeding user menu option is repeated until imaging according to all the registered user menu options in the user page 56 is completed, in the step S26.

As described heretofore, the succeeding user menu option 82 is displayed in an overlapped manner with the radiation image 65A after displaying the radiation image 65A on the touchscreen display unit 31a in the embodiment. Initially, only the radiation image 65 is displayed on the touchscreen display unit 31a. No reduction of a display size of the radiation image 65A is required. The radiation image 65A is not hidden by other visual objects. Consequently, the radiation image 65A can be displayed with improved recognition. Furthermore, the succeeding user menu option 82 is displayed after displaying the radiation image 65A, so that a succeeding radiation image can be previewed without leaving hands from the animal body P. As the succeeding user menu option 82 is displayed in an overlapped manner with the radiation image 65A, both of the radiation image 65A and the succeeding user menu option 82 can be displayed simultaneously even without reducing their display sizes. The radiation image 65A and the succeeding user menu option 82 can be visually checked even from a point distant to the portable console device 31, because the radiation image 65A and the succeeding user menu option 82 can be displayed with improved recognition.

Also, the succeeding user menu option 82 is displayed in an overlapped manner with the pass-through area 65B of the radiation image 65A. The radiation image 65A is not hidden by the succeeding user menu option 82 but appears visibly.

Figure 18:
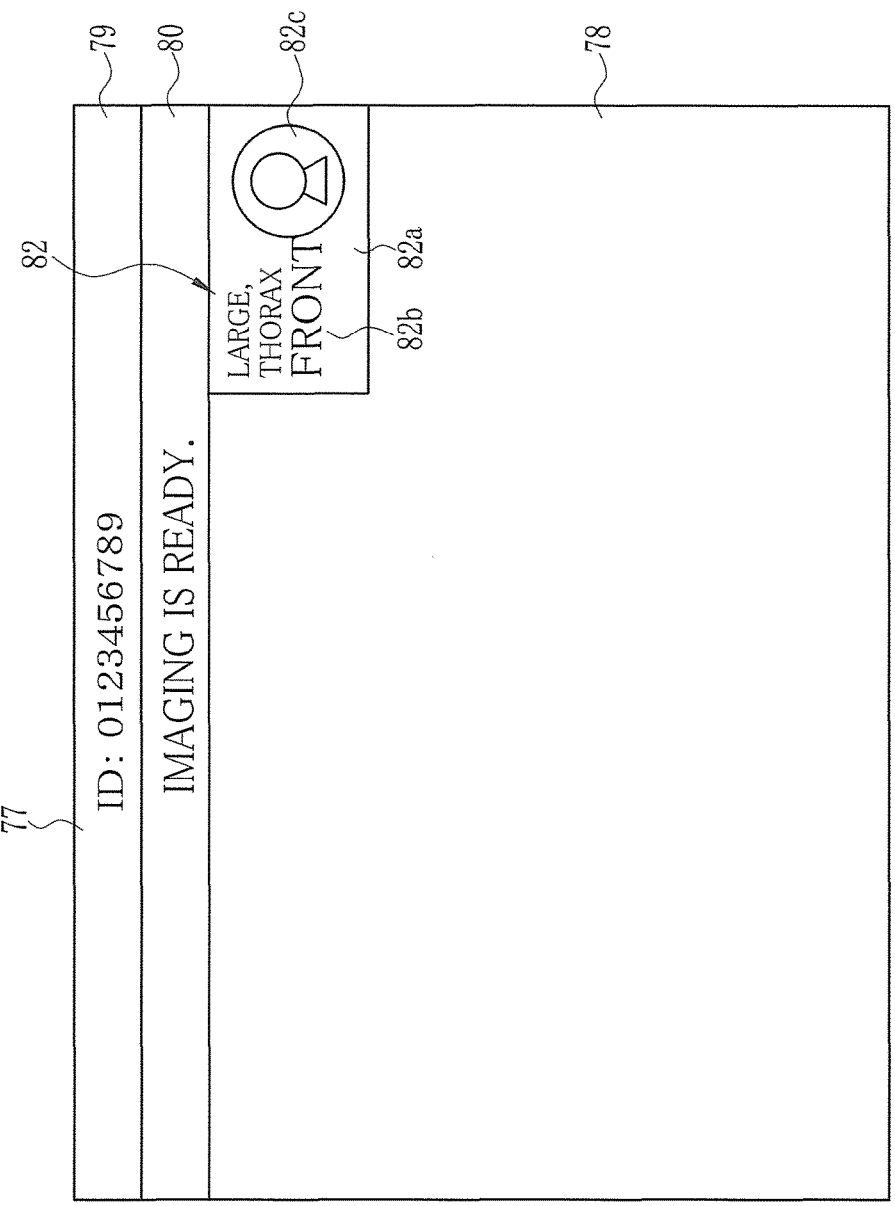
FIG. 18 is a plan illustrating a view page only with the succeeding user menu option.

In the embodiment, the succeeding user menu option 82 is displayed upon the lapse of waiting time of display after the radiation image 65A becomes displayed. However, the user menu option 62 or 63 touched by long press can be displayed by way of the succeeding user menu option 82 for the image display area 78 before displaying a radiation image in response to changeover from the user page 56 to the view page 77 by the long press of the user menu option 62 or 63 before imaging. See FIG. 18. It is therefore possible to view the succeeding user menu option even immediately after changeover from the user page 56 to the view page 77.

In the present embodiment, the succeeding user menu option 82 is displayed in an overlapped manner with the pass-through area 65B of the radiation image 65A. However, at least part of the succeeding user menu option 82 or the entirety of the succeeding user menu option 82 can be displayed in an overlapped manner with the radiation image 65A. After the lapse of the waiting time for displaying the radiation image 65A, the succeeding user menu option 82 becomes displayed. Even assuming that the entirety of the succeeding user menu option 82 is displayed in an overlapped manner with the radiation image 65A, both of the radiation image 65A and the succeeding user menu option 82 can be viewed and checked safely. Furthermore, it is possible to change a shape, display position and other forms of the succeeding user menu option 82 for containment within the pass-through area 65B in compliance with the form of the pass-through area 65B.

Figure 19:
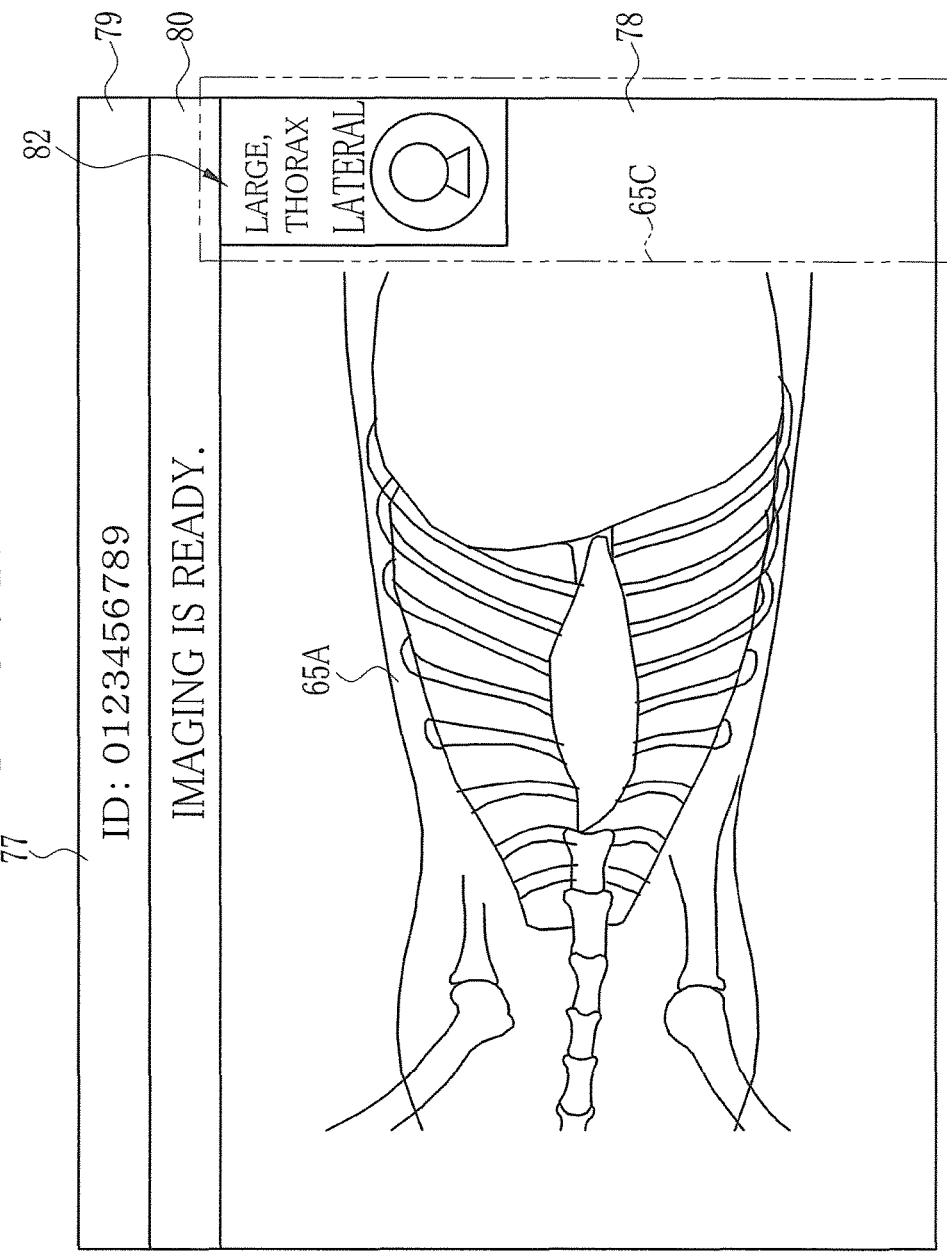
FIG. 19 is a plan illustrating a view page in which a form for the succeeding user menu option is changeable according to a pass-through area.

In FIG. 19, an example of changing a direction of the radiation image 65A is illustrated. The radiation image 65A is enlarged and displayed. A pass-through area 65C is formed in a smaller size than the pass-through area 65B described above. The display controller 42 changes a display form of the succeeding user menu option 82 into a vertically long form in consideration of the shape of the pass-through area 65C, so that the succeeding user menu option 82 can be contained within the pass-through area 65C. It is therefore possible to display the radiation image and succeeding user menu option without lowering visual recognition even with a small form of the pass-through area of the radiation image. Note that a display position of the succeeding user menu option 82 is not limited to the upper right portion of the radiation image 65A, but can be disposed in other suitable manners without lowering visual recognition of the radiation image 65A. The pass-through area 65C can be recognized by a well-known technique of image recognition.

In the present embodiment, the exclusion processing of a radiation image is performed in response to manual operation of the exclusion button 84b. However, it is possible to perform the exclusion procession by detecting exact correspondence between a displayed radiation image in the view page 77 and a user menu option, in a manner similar to the use of the exclusion button 84b.

Figure 20:
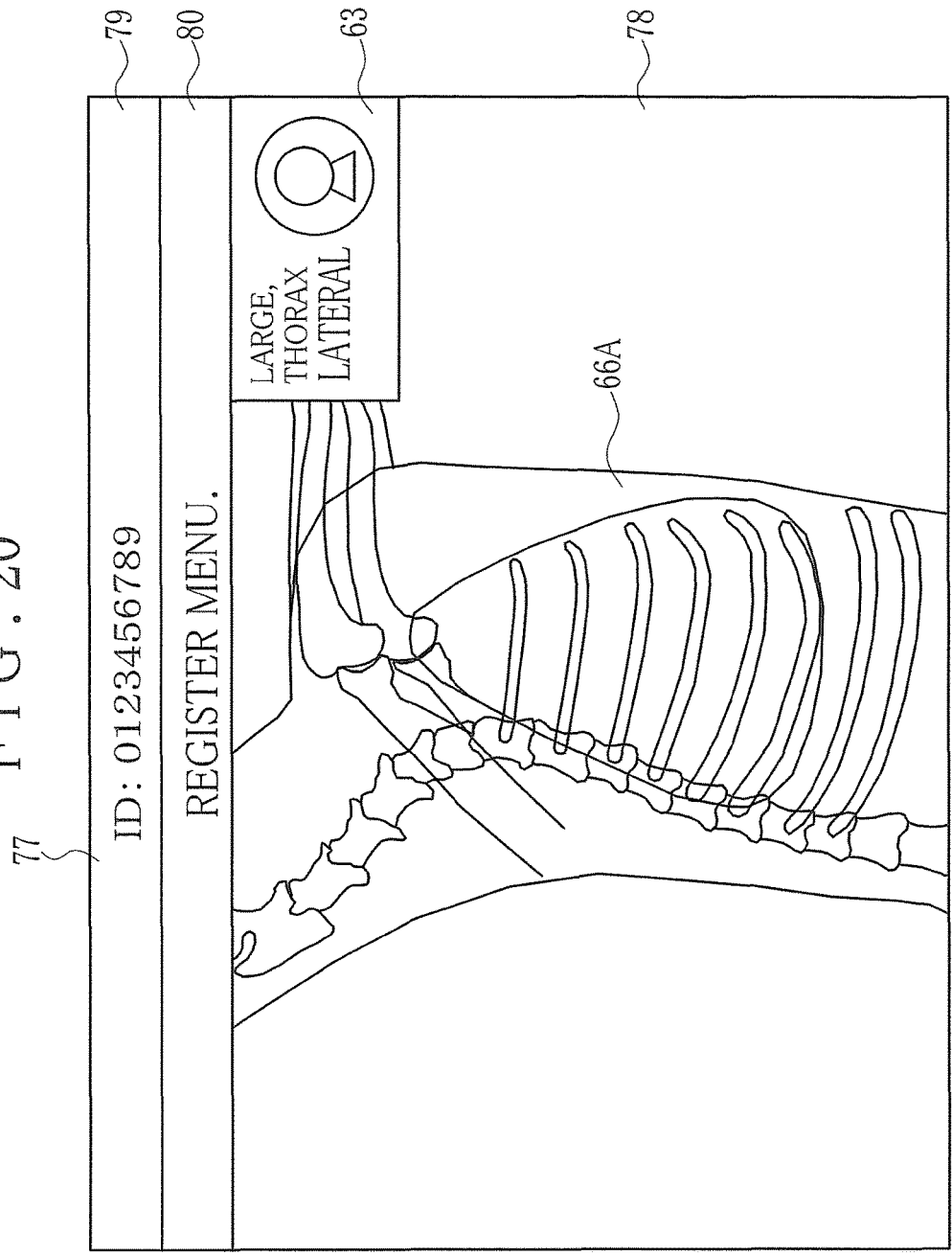
FIG. 20 is a plan illustrating a view page in a state for exclusion processing in which the radiation image corresponds to the user menu option.

Specifically, a flicking action is conducted while the radiation image 66A is displayed in the view page 77, to change the user menu option. The user menu option 63 for the radiation image 66A after the imaging is displayed in the view page 77. See FIG. 20. The user menu option 63 of the radiation image 66A after the imaging corresponds to a current user menu option. In short, flicking changes over the succeeding user menu option to the current user menu option. Thus, the radiation image 66A displayed in the view page 77 comes to correspond to the current user menu option 63. The radiation image 66A is set as an excluded image to perform the exclusion processing.

Figure 16:
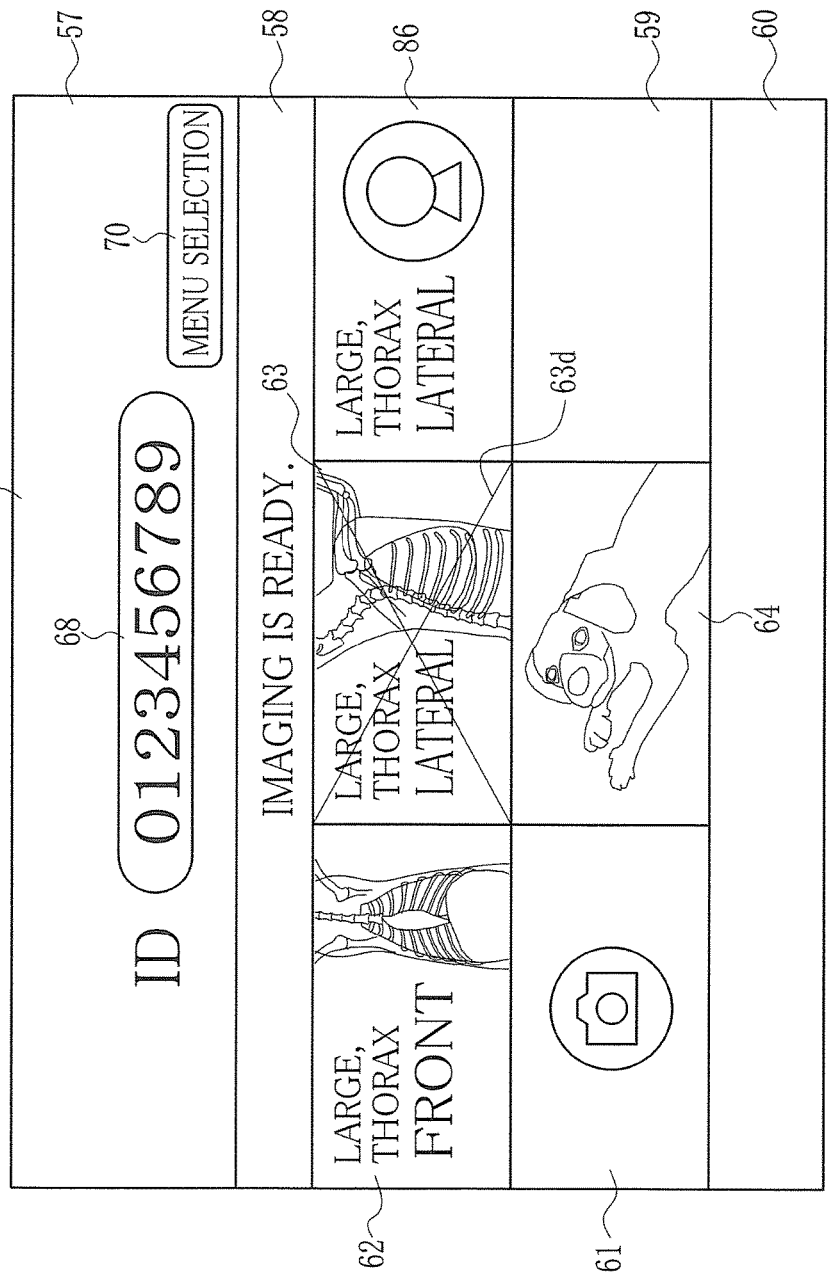
FIG. 16 is a plan illustrating the user page in a state for exclusion processing.

In FIG. 16, the exclusion processing unit 48 causes the user menu option 63 for the radiation image 66A as excluded image to display the diagonal lines 63d (cancel lines) in the user page 56. Also, the user menu option 86 for re-imaging is automatically registered after setting the same animal type information and imaging information as the excluded image, and is displayed in the sample window area 59. Note that the condition of the user menu option 86 registered newly for re-imaging is the same as the condition of the current user menu option. Registering the user menu option 86 for re-imaging means possibility of re-imaging in the radiation image detector 30 according to the current user menu option. The portable console device 31 transmits the animal type information and imaging information of the user menu option 86 for re-imaging to the radiation image detector 30. Thus, it is possible easily to perform re-imaging of the excluded image.

Second to sixth preferred embodiments of the invention are hereinafter described. Elements similar to those of the first embodiment are designated with identical reference numerals.

Second Embodiment

For display processing of a succeeding user menu option, a preview image is utilized in addition to a main image or radiation image detected by radiographic imaging for the purpose of rapidity in displaying a radiation image. In FIG. 21, a radiographic imaging device 90 includes a radiation image detector 93 and the portable console device 31. The radiographic imaging device 90 detects a main image 91, forms a preview image 92 on the basis of the main image 91, and transmits the main image 91 and the preview image 92. The portable console device 31 receives the main image 91 and the preview image 92. The preview image 92 is formed by reducing a size of the main image 91 or by lowering image quality of the main image 91, and has a smaller data size than the main image 91. Time required for transmitting the preview image 92 is shorter than that for the main image 91. Thus, reception of the preview image 92 at the portable console device 31 is completed more rapidly than that of the main image 91.

Figure 22:
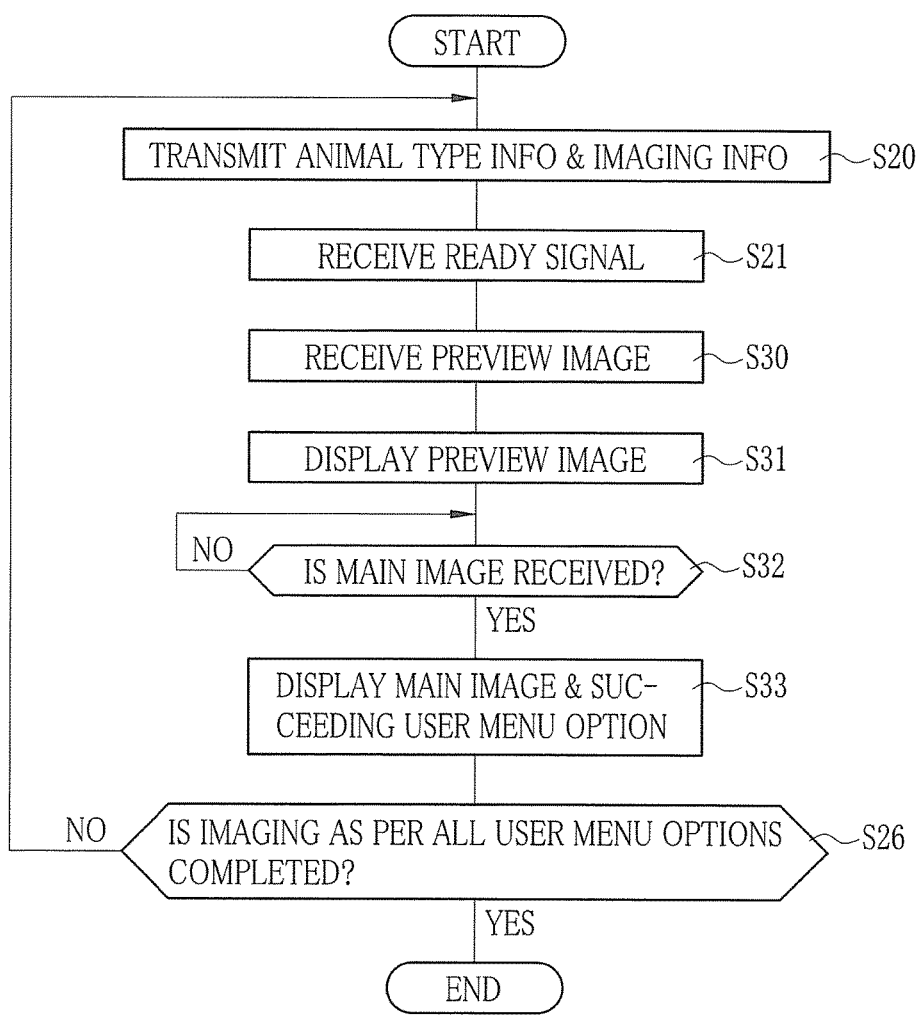
FIG. 22 is a flow chart illustrating radiation image retrieval.

In FIG. 22, radiation image retrieval in the display controller 42 of the portable console device 31 is illustrated. After completing the transmission of the animal type information and imaging information (S20) and the reception of the ready signal (S21), radiation is irradiated actually and a radiation image is created, in the same manner as the first embodiment. The display controller 42 receives the preview image 92 from the radiation image detector 93 in the step S30. In FIG. 23, the display controller 42 causes the view page 77 to display the preview image 92 in the step S31. The display controller 42 upon receiving the main image 91 from the radiation image detector 93 (yes in the step S32) performs display processing to display the succeeding user menu option 82 in the view page 77 in an overlapped manner with the main image 91 upon changeover from the preview image 92 to the main image 91, in the step S33. The succeeding user menu option 82 is displayed in an overlapped manner with a pass-through area of the main image 91, in the same manner as the first embodiment.

In the present embodiment, only the preview image 92 is displayed initially on the touchscreen display unit 31a. Thus, the preview image 92 (radiation image) can be displayed with improved recognition, as no reduction in a display size of the preview image 92 is required, and the preview image 92 is not hidden by other displayed objects. Upon changeover of display from the preview image 92 to the main image 91, the succeeding user menu option 82 is displayed on the touchscreen display unit 31a together with the main image 91. Thus, a form of a succeeding radiation image can be checked without leaving the veterinarian's hands from the animal body P.

In this situation, time (time lag) taken after displaying the preview image 92 and before displaying the succeeding user menu option 82 depends upon time required for receiving the main image 91. The time (time lag) is not a predetermined value in the manner of waiting time for display described in the first embodiment above, but is changeable according to an environmental factor, such as a transmission speed. In the case of good environment of excessively short time before receiving the main image 91, it is possible to display the main image 91 and the succeeding user menu option 82 upon the lapse of the waiting time of the display predetermined in the manner of the first embodiment, as an example of a limit value for receiving the main image 91. In combination with this operation, a preferable value of the waiting time of display can be equal to or longer than time for visually recognizing the preview image 92.

The succeeding user menu option 82 is displayed in an overlapped manner with the main image 91. The main image 91 and the succeeding user menu option 82 can be displayed simultaneously even without reducing their display sizes. The main image 91 and the succeeding user menu option 82 can be displayed on the touchscreen display unit 31a with improved recognition, and can be visually checked and confirmed from a person positioned remotely from the portable console device 31. The veterinarian or operator can confirm the positioning of the animal body with the preview image 92 without problem. The main image 91 and the succeeding user menu option 82 become displayed during preparation for re-imaging. Thus, the re-imaging can be performed after checking the main image 91 and the succeeding user menu option 82.

Third Embodiment

In the image browsing for human medicine, conditions for required radiation images may be predetermined as standard conditions for various purposes of the image browsing, for example, body parts, imaging directions and the like. Assuming that the purpose is diagnosis of a lung cancer of a person, radiation images are created generally in plural imaging directions of the front, lateral and diagonal for a chest as a body part of interest. In order to perform the image browsing reliably without errors in the predetermined conditions, sub menu items for retrieving radiation images of the plural body parts and plural imaging directions can be predetermined in a set (group). To this end, a console device is constructed to register the set of the sub menu items as a user menu option. A third preferred embodiment is to display the set of the sub menu items as a succeeding user menu option.

Figure 24:
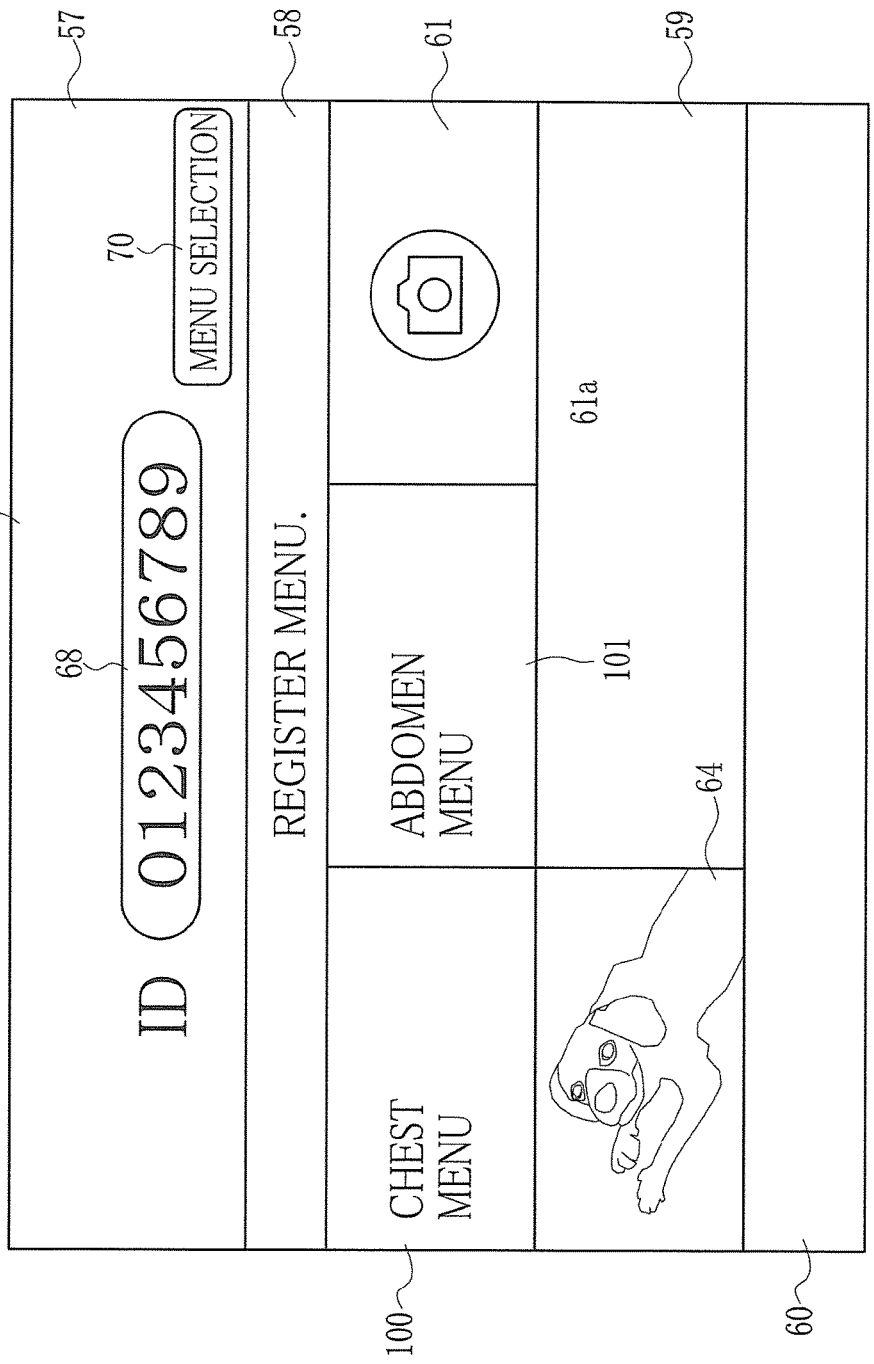
FIG. 24 is a plan illustrating a view page of a third preferred embodiment.
Figure 25:
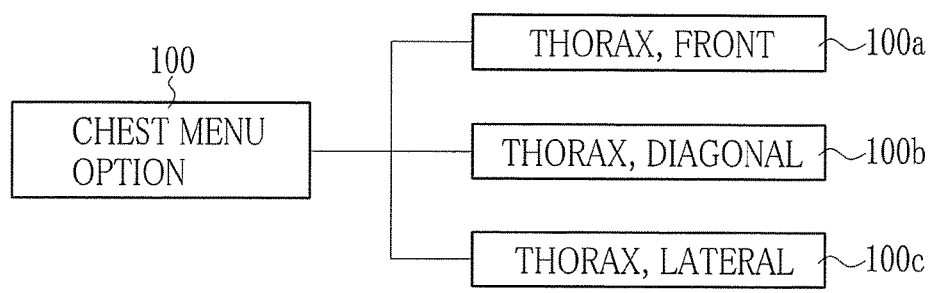
FIG. 25 is a block diagram schematically illustrating a chest menu option.
Figure 26:
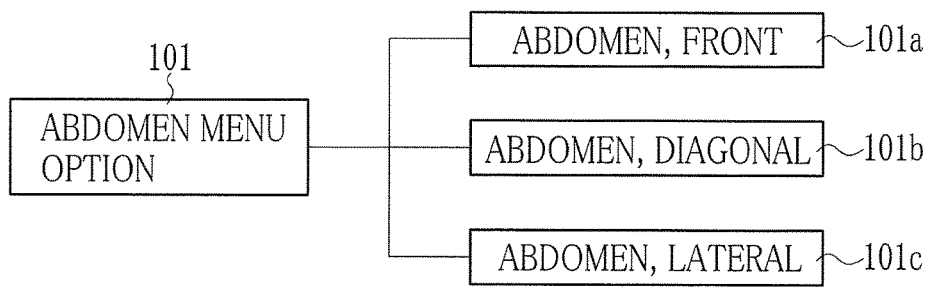
FIG. 26 is a block diagram schematically illustrating an abdomen menu option.

In the user page 56 in FIG. 24, a chest menu option 100 and an abdomen menu option 101 are registered as user menu options by menu registration and displayed in the sample window area 59. The chest menu option 100 is for the purpose of diagnosing a lung cancer. The abdomen menu option 101 is for the purpose of diagnosing a gastric cancer. In FIG. 25, plural sub menu items 100a, 100b and 100c are predetermined in the chest menu option 100 for a body part of "THORAX" and imaging directions of "FRONT", "DIAGONAL" and "LATERAL". In FIG. 26, plural sub menu items 101a, 101b and 101c are predetermined in the abdomen menu option 101 for a body part of "ABDOMEN" and imaging directions of "FRONT", "DIAGONAL" and "LATERAL".

Assuming that the display controller 42 receives a radiation image created according to the sub menu item 100a at a first location in the chest menu option 100, a radiation image 103 is displayed in the view page 77 as illustrated in FIG. 27. Upon lapse of the waiting time for display from displaying the radiation image 103, the sub menu items 100b and 100c in the chest menu option 100 are displayed in an overlapped manner with the radiation image 103 as a succeeding user menu option. At each time that the display controller 42 receives a radiation image created according to one of the sub menu items, the received radiation image is displayed in the view page 77. Upon lapse of the waiting time for display, the display controller 42 performs display processing to display the remainder of the sub menu items.

Upon receiving a radiation image according to the sub menu item 100c of a final location in the chest menu option 100, the display controller 42 causes the view page 77 to display a received radiation image 105. Upon lapse of the waiting time for display, the display controller 42 performs display processing of the sub menu items 101a-101c in the abdomen menu option 101 in an overlapped manner with the radiation image 105 for a form of a succeeding user menu option. In short, the display controller 42 causes the view page 77 to display plural sub menu items in a set by way of a succeeding user menu option in a list form.

In the embodiment, the sub menu items 100a-100c and the sub menu items 101a-101c are displayed in a list form as a succeeding user menu option for each of the sets of the chest menu option 100 and the abdomen menu option 101. A radiation image can be previously checked with requirement for the image browsing according to the set of the menu items, to increase efficiency in the operation. Only sub menu items before imaging are displayed in the view page 77 according to the progress of the imaging. A succeeding radiation image to be created can be previously checked.

Fourth Embodiment

Figure 28:
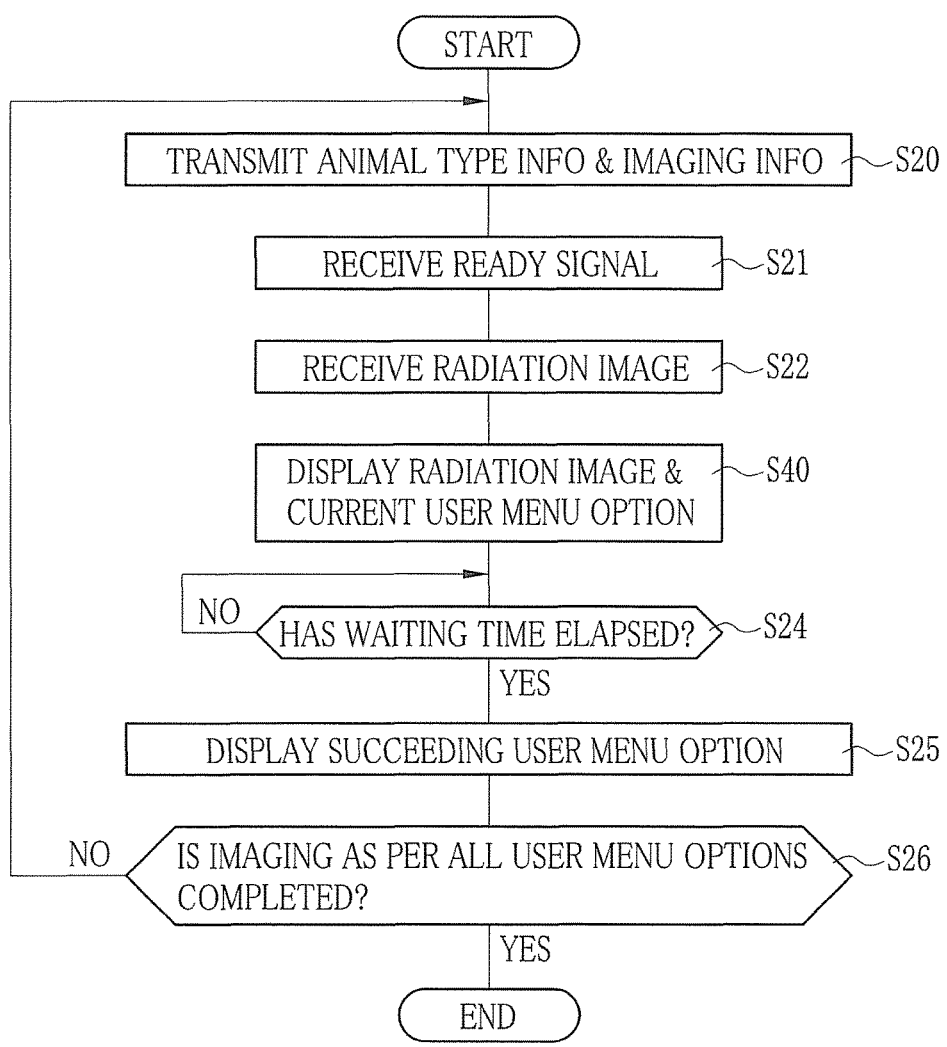
FIG. 28 is a flow chart illustrating radiation image retrieval of a fourth preferred embodiment.

For display processing of the view page 77, the current user menu option of the displayed radiation image is displayed in an overlapped manner with the radiation image together with the succeeding user menu option. In FIG. 28, the portable console device 31 in the radiation image retrieval performs tasks of transmission of animal type information and imaging information in the step S20, reception of a ready signal in the step S21, and reception of a radiation image in the step S22, in a manner similar to the first embodiment.

In FIG. 29, the display controller 42 causes the view page 77 to display the radiation image 65A from the radiation image detector 30 and a current user menu option 110 or radiation image retrieving menu option in an overlapped manner with the radiation image 65A in the step S40, the current user menu option 110 being registered for retrieving the radiation image 65A. A pass-through area 65D is formed in an upper left portion of the radiation image 65A. The current user menu option 110 is overlapped with the pass-through area 65D. The current user menu option 110 includes a display area 110a and alphanumeric information 110b. The display area 110a extends horizontally in a form of a rectangular quadrilateral. The alphanumeric information 110b is displayed in the display area 110a. The alphanumeric information 110b expresses animal type information and imaging information set upon registering the current user menu option 110.

The display controller 42 checks whether the waiting time for display has elapsed or not in the step S24 after displaying the radiation image 65A in the image display area 78. Assuming that the waiting time has elapsed (yes in the step S24) after displaying the radiation image 65A, the display controller 42 performs display control to display the succeeding user menu option 82 in an overlapped manner with the radiation image 65A in the step S25. Processing for the purpose of displaying the succeeding user menu option is repeated until completing the imaging for all of the user menu options registered in the user page 56, in the step S26.

In the embodiment, the current user menu option 110 registered to retrieve the radiation image 65A is displayed in an overlapped manner with the radiation image 65A. It is possible to check the menu option according to which the radiation image 65A has been retrieved. The current user menu option 110 is displayed in an overlapped manner with the pass-through area 65D of the radiation image 65A, which is not hidden by the current user menu option 110. In the embodiment, the current user menu option 110 is displayed in the pass-through area 65D. However, the current user menu option 110 can be displayed at any location, for example, under the succeeding user menu option 82 in the pass-through area 65B on the right side of the radiation image 65A in FIG. 14.

Fifth Embodiment

For display processing of a current user menu option, a preview image is utilized in addition to a main image in a manner similar to the second embodiment. In FIG. 21, the radiographic imaging device 90 includes the radiation image detector 93 and the portable console device 31. The radiation image detector 93 transmits the main image 91 and the preview image 92. The portable console device 31 receives the main image 91 and the preview image 92. The preview image 92 has a smaller data size than the main image 91, so transmission of the preview image 92 is more rapid than that of the main image 91, in the same manner as the second embodiment.

Figure 30:
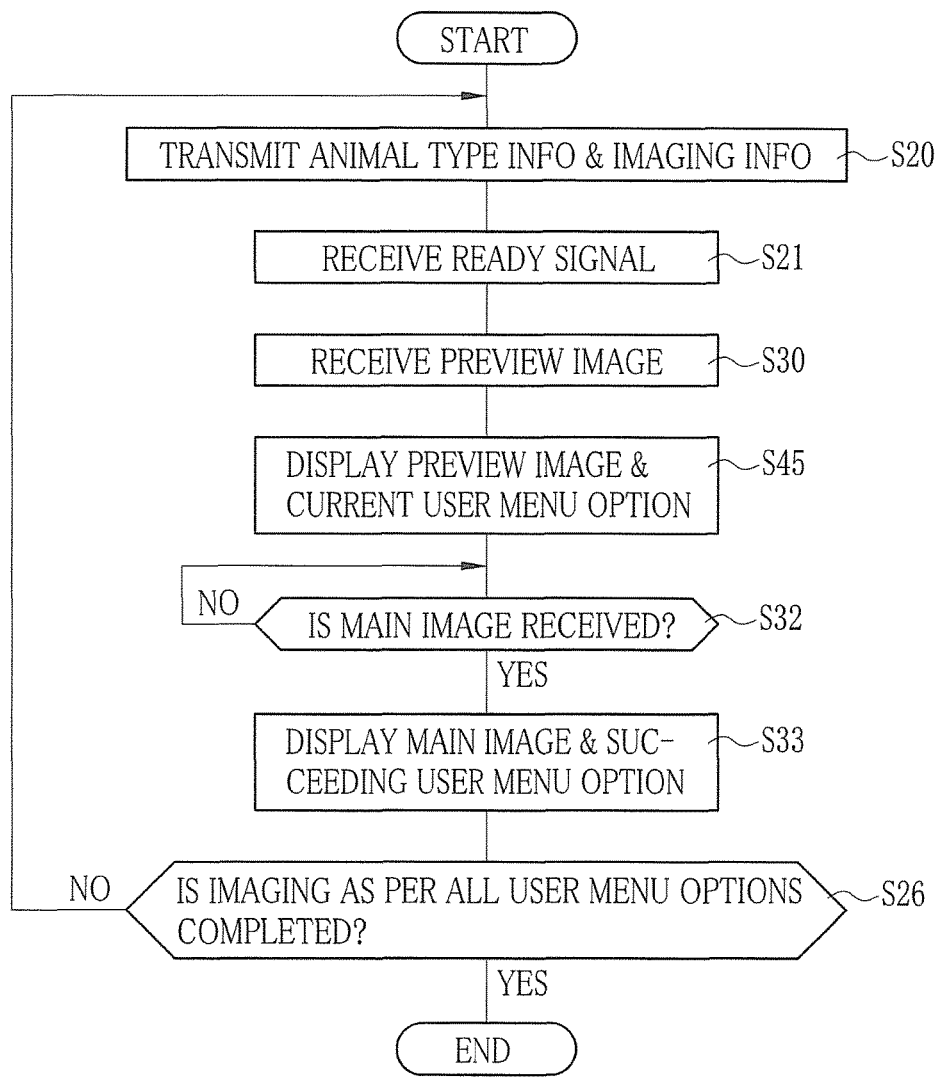
FIG. 30 is a flow chart illustrating radiation image retrieval of a fifth preferred embodiment.

In FIG. 30, the display controller 42 in the portable console device 31 performs tasks in the radiation image retrieval in the same manner as the second embodiment, the tasks including transmission of animal type information and imaging information (S20), reception of a ready signal (S21) and reception of the preview image 92 (S30). In FIG. 31, the display controller 42 causes the view page 77 to display the preview image 92 (from the radiation image detector 30) and a current user menu option 115 or radiation image retrieving menu option in an overlapped manner with the preview image 92 in the step S45, the current user menu option 115 being registered for retrieving the preview image 92. A pass-through area is formed on a left side of the preview image 92. The current user menu option 115 is overlapped with the pass-through area in the same manner as the fourth embodiment. The display controller 42 upon receiving the main image 91 from the radiation image detector 93 (yes in the step S32) causes the view page 77 to display the main image 91 and the succeeding user menu option 82 in place of the preview image 92 and the current user menu option 115 in the step S33. The succeeding user menu option 82 is displayed in an overlapped manner with a pass-through area on a right side of the main image 91 in the same manner as the first embodiment.

In the embodiment, the current user menu option 115 registered for retrieving the preview image 92 is displayed with the preview image 92. It is possible visually to find a user menu of an origin of the preview image 92 displayed currently in relation to the user menu option. Upon changeover from the preview image 92 to the main image 91, the succeeding user menu option 82 is displayed. It is possible to preview a succeeding radiation image without leaving hands from the animal body P.

Sixth Embodiment

In the fourth and fifth embodiments, the current user menu option is displayed. In contrast, attribute information of a created radiation image is utilized to display information of the current user menu option in the present embodiment.

Figure 32:
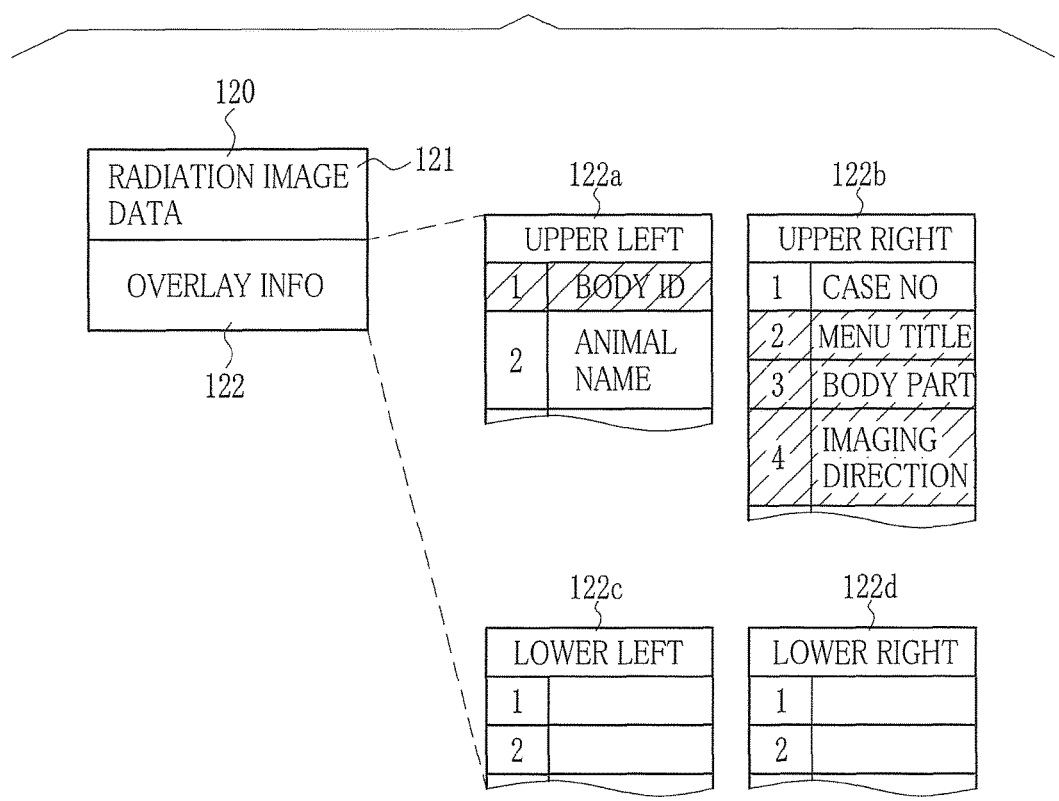
FIG. 32 is a block diagram schematically illustrating overlay information of a sixth preferred embodiment.

Data of radiation images detected by the radiation image detector 30 is in a file format according to the DICOM (Digital Imaging and Communication in Medicine) as standards of formats and communication protocol of medical images. In FIG. 32, a radiation image file 120 in the DICOM has radiation image data 121 and overlay information 122, which is displayable in an overlapped manner with a radiation image while the radiation image is displayed by the console device. The overlay information 122 includes information items for locations in the overlapped form with the radiation image, the items including an upper left portion 122a, an upper right portion 122b, a lower left portion 122c and a lower right portion 122d. The upper left portion 122a of the overlay information 122 has a body ID, animal name and the like. The upper right portion 122b of the overlay information 122 has a case number, menu title of imaging, and the like.

Figure 33:
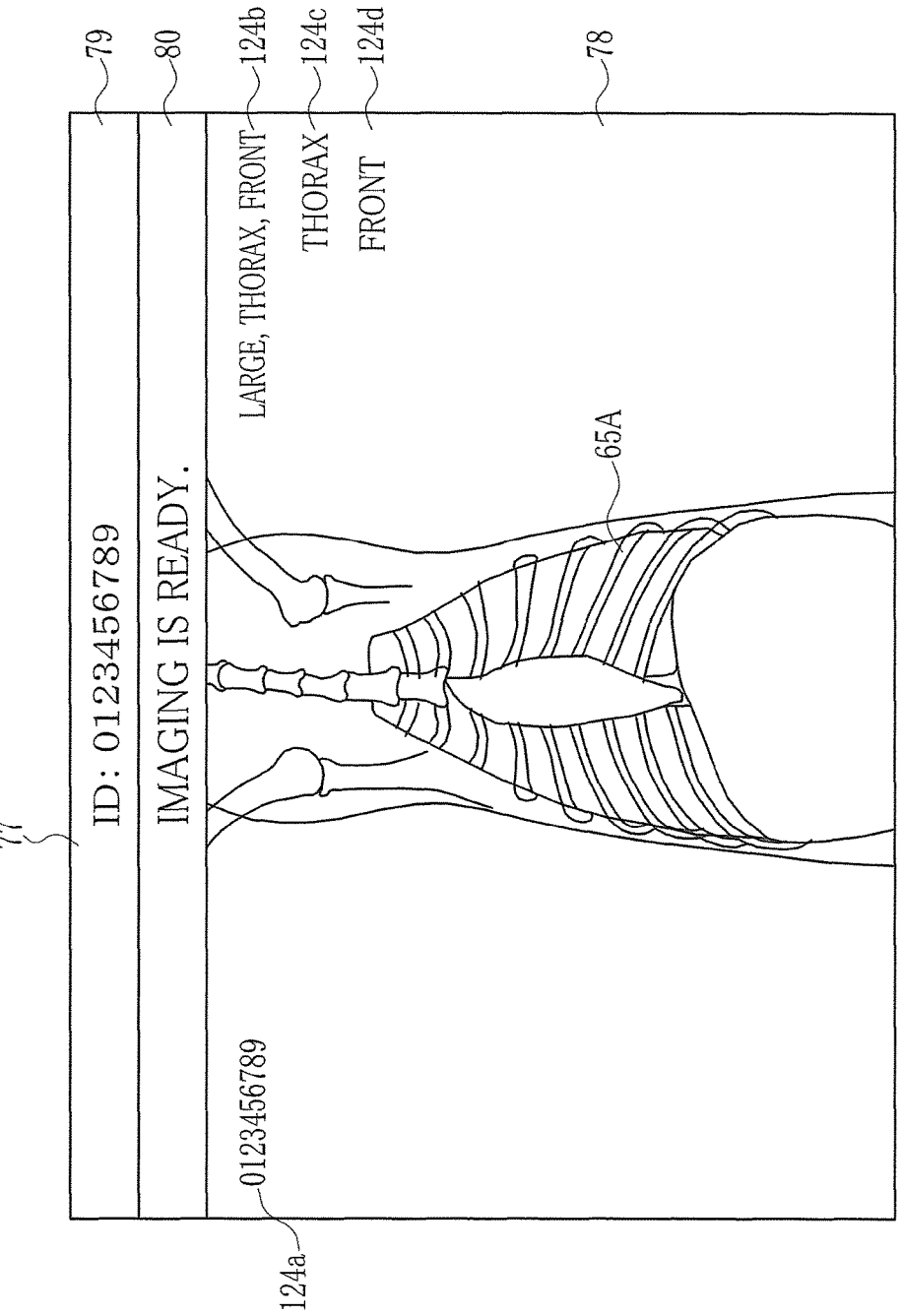
FIG. 33 is a plan illustrating a view page.

In FIG. 33, the display controller 42 of the portable console device 31 causes the view page 77 to display items of the overlay information 122 in an overlapped manner with the radiation image in place of the current user menu option in the course of displaying the radiation image and the user menu option. It is unnecessary to display the entirety of the overlay information 122. Only partial items in the overlay information 122 relevant to the current user menu option are displayed. In FIG. 33, a body ID 124a is displayed in an upper left portion of the radiation image 65A. A menu title 124b, a body part 124c and an imaging direction 124d are indicated in an upper right portion of the radiation image 65A. Consequently, it is possible to check the user menu option according to which the displayed radiation image has been retrieved, in the same manner as displaying the current user menu option.

Seventh Embodiment

Figure 34:
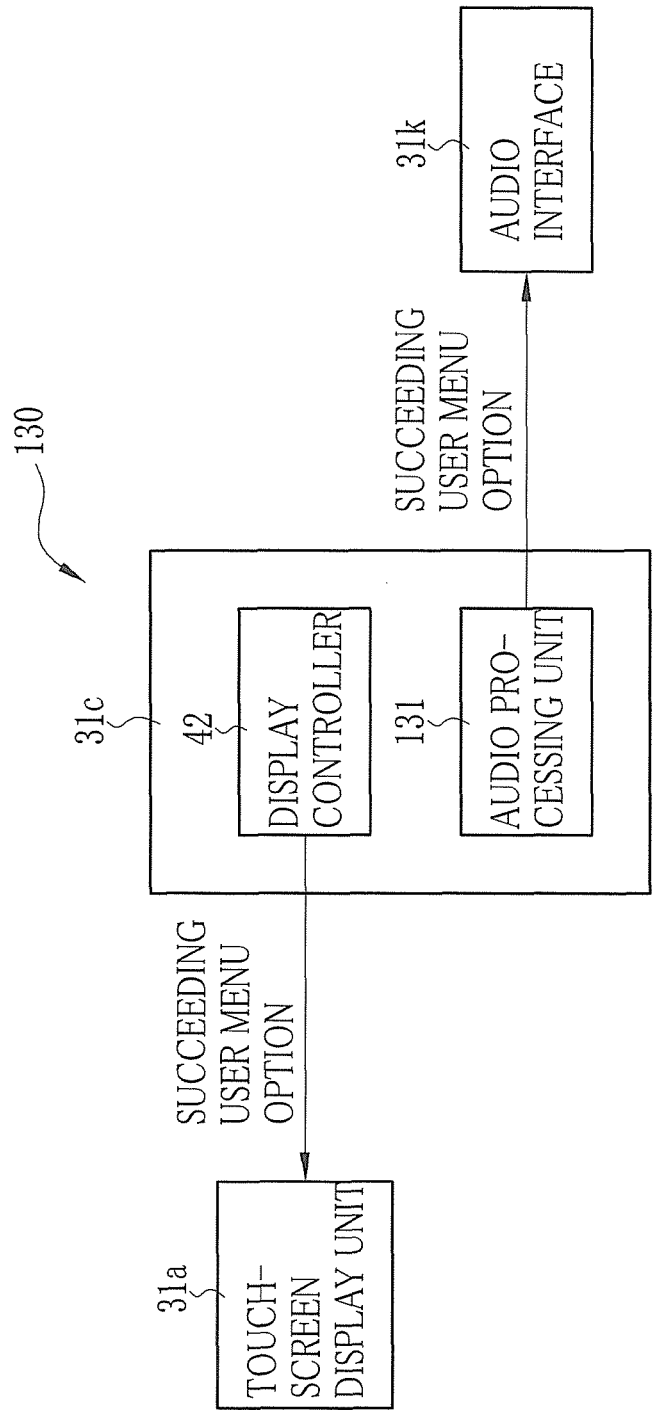
FIG. 34 is a block diagram schematically illustrating a portable console device of a seventh preferred embodiment.

A succeeding user menu option according to a seventh embodiment is expressed by use of sound or voice. In FIG. 34, a portable console device 130 includes the CPU 31c. The display controller 42 and an audio processing unit 131 are caused to operate in the CPU 31c upon running the computer-executable program. The audio processing unit 131 outputs sound of the succeeding user menu option from the audio interface 31k for the display controller 42 to perform display processing of the succeeding user menu option on the touchscreen display unit 31a. The sound can be reproduced sound created by playing back audio data of previously recorded sound or voice of a person, or synthesized sound of audio data generated by the CPU 31c. In the embodiment, it is possible acoustically to confirm the succeeding user menu option of the sound output by the audio interface 31k. Operability can be made higher in the course of imaging of plural radiation images while the posture of the animal body P is changed.

Eighth Embodiment

Figure 35:
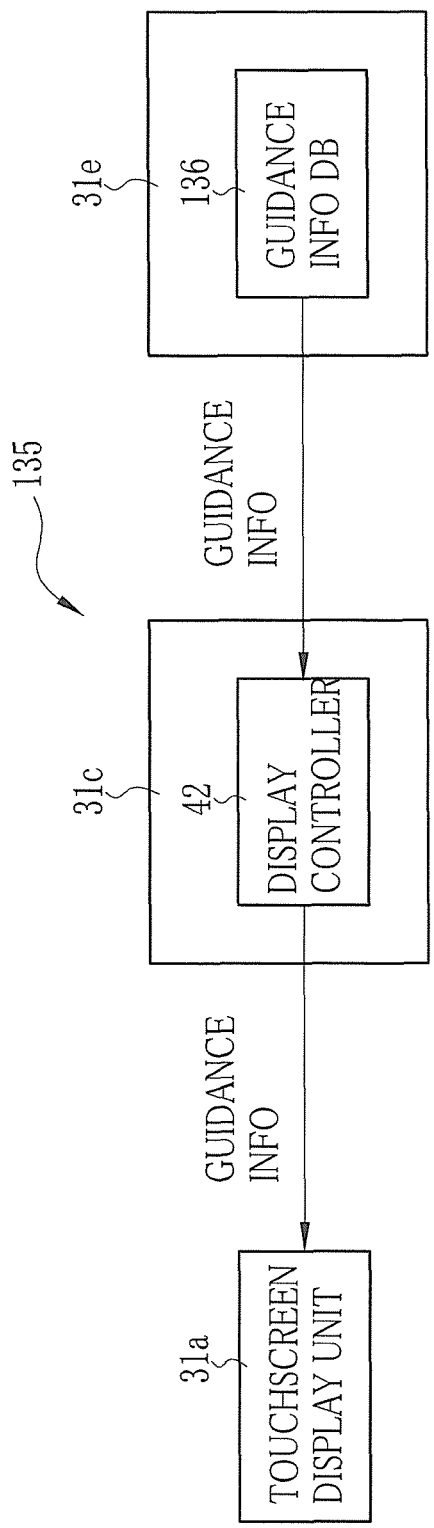
FIG. 35 is a block diagram schematically illustrating of a portable console device an eighth preferred embodiment.

Guidance information is displayed in the image display area 78 before displaying a radiation image upon changeover from the user page 56 to the view page 77 by long press on the user menu option 62 or 63. In FIG. 35, a portable console device 135 has the storage medium 31e, which is constituted by a guidance information database 136 or guidance information storage medium for storing plural sets of guidance information related to steps of imaging of a radiation image of the animal body P. The sets of the guidance information are prepared for respectively the animal types of the animals having the animal body P, and include a guide image and a help text. Examples of the guide image are a still image such as a photograph and drawing, and a moving image such as a video image or animation image.

In FIG. 36, the display controller 42 responds to changeover from the user page 56 to the view page 77 by long press of the user menu option 62 or 63 before imaging, and reads out guidance information 138 or help information from the guidance information database 136 according to the selected one of the user menu options 62 and 63, and causes the image display area 78 to display the guidance information 138. The guidance information 138 in the image display area 78 includes guide images 139a and 140a and help texts 139b and 140b, predetermined for plural steps of imaging.

An example of the help text 139b is as follows.

"Place the electronic cassette on the patient table. Hold limbs of a rabbit by hands of 2 persons. In case of resistance of the rabbit, stop and start placement again.

NB. A rabbit has behavior of accepting repeated stimulus, and becomes accustomed to the posture by the repetition of the action."

An example of the help text 140b is as follows.

"Turn round the rabbit laterally while keeping the body placed on the electronic cassette. Pull the limbs forwards and backwards to extend the body. Direct its backbone in parallel with the electronic cassette."

Should the guidance information 138 be not displayable entirely in the image display area 78, the image display area 78 is caused to appear in a scrollable manner. Upon receiving a radiation image from the radiation image detector 30, the received radiation image is displayed in the image display area 78 in place of the guidance information 138. It is possible in the embodiment to utilize the image display area 78 without information immediately after changeover of the pages. As the guidance information 138 is displayed in the image display area 78, imaging of a radiation image can be performed suitably by following the guidance information 138.

Ninth Embodiment

Figure 37:
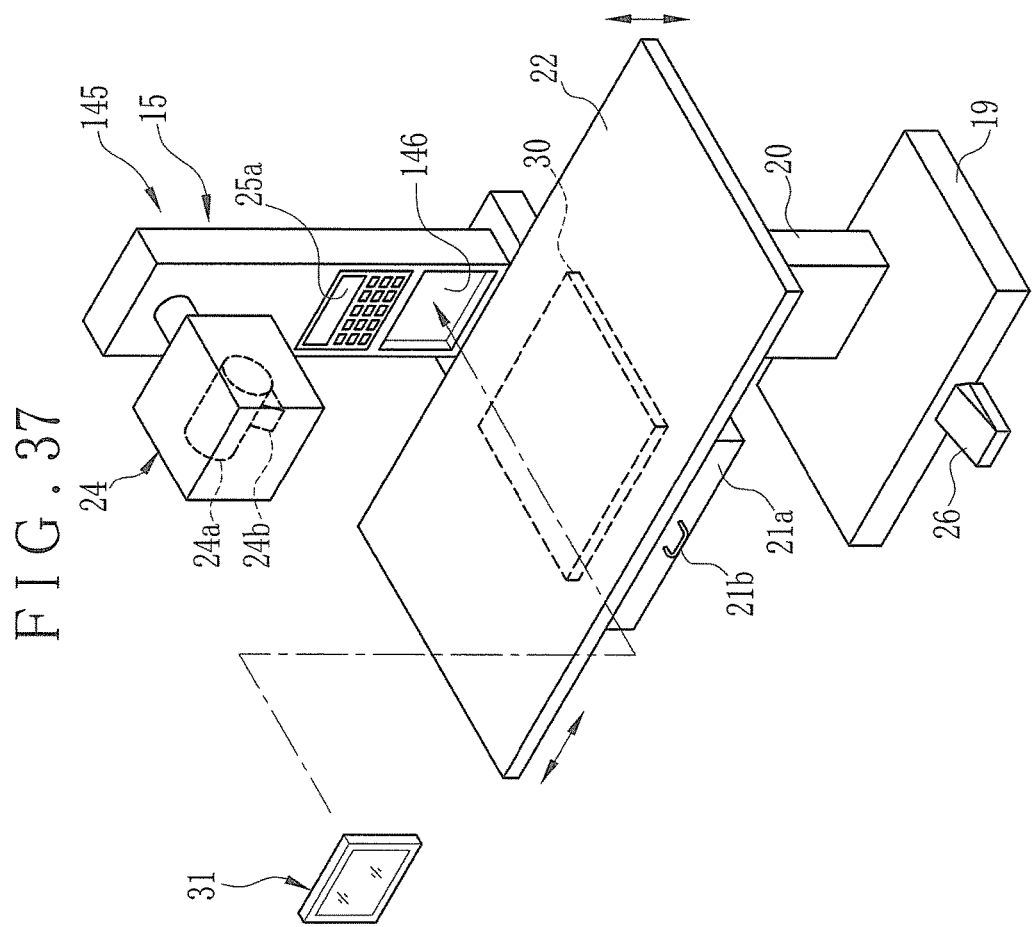
FIG. 37 is a perspective view illustrating a radiographic imaging system of a ninth preferred embodiment.

The portable console device 31 in the first embodiment is disposed on the patient table 22 of the stand device 15 or a support plate near to the stand device 15. In FIG. 37, another preferred radiographic imaging system 145 is illustrated. A console holder 146 is disposed in the stand 20 of the stand device 15 for receiving insertion of the console housing of the portable console device 31 for positioning near to the control panel 25a of the source driver 25. This is effective in facilitating visual recognition of the portable console device 31 as the portable console device 31 is held on the portion of the stand device 15. Also, the portable console device 31 and the control panel 25a can be manually operated without leaving from the stand device 15, because the portable console device 31 is set near to the control panel 25a. Note that the nearness to the control panel 25a means such a distance that a veterinarian ID can manipulate both of the portable console device 31 and the control panel 25a while he or she manually touches the animal body P without leaving.

In the above embodiments, the basis of the portable console device 31 is the tablet terminal device. However, a basis of the portable console device 31 in the invention can be a notebook personal computer, smart phone, and other user terminal devices. In the above embodiments, the portable console device 31 is for the veterinary use. However, the portable console device 31 of the invention can be used for medicine for human patients, for example, emergency medicine.

In the above embodiments, the console device retrieves radiation images from the radiographic imaging device having the FPD. However, a console device can retrieve radiation images from other apparatuses or data sources, such as X-ray film scanner or IP reading device for use with an X-ray film, IP cassette, or the like.

Note that the user menu options or radiation image retrieving menu options of the present invention are not limited to the above embodiments, but can be other structure in a list form well-known in the display processing, such as a selection list, navigation area, tool bar, button display area and the like.

In one preferred embodiment mode of the invention, a computer executable program for a portable information terminal device for retrieving a radiation image created by a radiographic imaging device is provided. A program code is for registering plural user menu options for retrieving the radiation image. A program code is for retrieving the radiation image respectively according to the registered user menu options. A program code is for, after displaying the radiation image retrieved according to a current user menu option on a display unit among the user menu options, performing display processing to display a succeeding user menu option for retrieving at least a succeeding radiation image in an overlapped manner with the displayed radiation image.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A console device of a portable type for retrieving a radiation image created by a radiographic imaging device, comprising:
    a display unit;
    a processor, configured for:
        registering plural user menu options for configuring the radiographic imaging device to capture said radiation image and retrieving said radiation image, and retrieving said radiation image respectively according to said registered plural user menu options; and
    a display controller for, after displaying said radiation image retrieved according to a current user menu option on said display unit among said plural user menu options, performing display processing to display a succeeding user menu option for retrieving at least a succeeding radiation image later in an overlapped manner with said displayed radiation image.

2. A console device as defined in claim 1, wherein said display controller performs display processing of said succeeding user menu option upon lapse of waiting time for display after said radiation image becomes displayed.

3. A console device as defined in claim 1, wherein said display controller causes said display unit to display a main image of said radiation image and a preview image of said radiation image with a smaller data size than said main image in a sequence of changing over from said preview image to said main image;
    upon changing over said display unit from said preview image to said main image, said succeeding user menu option is displayed in an overlapped manner with said main image.

4. A console device as defined in claim 3, wherein said display controller causes said display unit to display said current user menu option in an overlapped manner with said preview image;
    upon changeover from said preview image to said main image, said succeeding user menu option is displayed in an overlapped manner with said main image.

5. A console device as defined in claim 4, wherein a pass-through area is formed in radiation image by directly receiving said radiation without passing through an object;
    said display controller performs display processing of said current user menu option or said succeeding user menu option inside said pass-through area.

6. A console device as defined in claim 5, wherein said display controller determines a display form of said current user menu option or said succeeding user menu option within said pass-through area by considering a form of said pass-through area.

7. A console device as defined in claim 1, wherein said succeeding user menu option includes a group of plural sub menu items, and said display controller performs display processing of said plural sub menu items by said group in a form of said succeeding user menu option.

8. A console device as defined in claim 7, wherein said display controller reads out attribute information associated with said radiation image before displaying said current user menu option, and causes display processing to display a first item in an overlapped manner with said current user menu option, said first item being relevant to said current user menu option among plural items included in said attribute information.

9. A console device as defined in claim 1, wherein said display controller performs display processing to display said current user menu option in an overlapped manner with said radiation image.

10. A console device as defined in claim 1, wherein when said display unit is changed over from displaying said succeeding user menu option to another user menu option, said processor is further configured for changing a sequence of retrieving said radiation image.

11. A console device as defined in claim 1, wherein when said succeeding user menu option is changed to a current user menu option, said processor is further configured for enabling said radiographic imaging device to perform re-imaging according to said current user menu option.

12. A console device as defined in claim 1, wherein said processor is further configured for changing for notifying information of said succeeding user menu option acoustically.

13. A console device as defined in claim 1, wherein said display controller causes said display unit to display guidance information for steps of creating said radiation image in said radiographic imaging device until said radiation image is initially retrieved according to said plural user menu options.

14. A control method for a portable information terminal device for retrieving a radiation image created by a radiographic imaging device, comprising steps of:
    registering plural user menu options for configuring the radiographic imaging device to capture said radiation image and retrieving said radiation image;
    retrieving said radiation image respectively according to said registered plural user menu options;
    displaying the radiation image retrieved for a current user menu option on a display unit; and
    after displaying said radiation image retrieved for said current user menu option on said display unit among said plural user menu options, displaying a succeeding user menu option for retrieving at least a succeeding radiation image later in an overlapped manner with said displayed radiation image.

15. A radiographic imaging system comprising:
    a radiographic imaging device for creating a radiation image from radiation passed through a body;
    a console device of a portable type for retrieving said radiation image from said radiographic imaging device; and
    a console holder for holding said console device;
    said console device including:
        a display unit;
        a processor configured for:
            registering plural user menu options for configuring the radiographic imaging device to capture said radiation image and retrieving said radiation image, and
            retrieving said radiation image respectively according to said registered plural user menu options; and
        a display controller for, after displaying said radiation image retrieved according to a current user menu option on said display unit among said plural user menu options, performing display processing to display a succeeding user menu option for retrieving at least a succeeding radiation image later in an overlapped manner with said displayed radiation image.

\* \* \* \* \*